(12) United States Patent
Lilley et al.

(10) Patent No.: US 6,803,394 B2
(45) Date of Patent: Oct. 12, 2004

(54) RADIATION CURABLE NAIL COATINGS AND ARTIFICIAL NAIL TIPS AND METHODS OF USING SAME

(75) Inventors: Pamela H. Lilley, Dewey, AZ (US); Sarah Peterson, Laurel, DE (US)

(73) Assignee: Gel Products, Inc., Laurel, DE (US)

( * ) Notice: Subject to any disclaimer, the term of this patent is extended or adjusted under 35 U.S.C. 154(b) by 119 days.

(21) Appl. No.: 10/154,235

(22) Filed: May 21, 2002

(65) Prior Publication Data

US 2003/0073753 A1 Apr. 17, 2003

Related U.S. Application Data

(63) Continuation-in-part of application No. 09/912,816, filed on Jul. 24, 2001, now Pat. No. 6,599,958, and a continuation-in-part of application No. 09/466,986, filed on Dec. 17, 1999, now Pat. No. 6,391,938, and a continuation-in-part of application No. 09/466,985, filed on Dec. 17, 1999, now abandoned, and a continuation-in-part of application No. 09/467,127, filed on Dec. 17, 1999, now Pat. No. 6,481,444.

(51) Int. Cl.$^7$ .............................. C08F 2/46; C08F 2/50
(52) U.S. Cl. ........................ 522/182; 522/96; 522/18; 522/64; 522/49; 522/50; 522/38; 522/120; 522/121; 522/151; 522/152; 522/172; 522/174; 424/61; 424/401; 252/181.13; 252/182.18; 252/182.22; 252/182.29
(58) Field of Search .................. 522/182, 96, 18, 522/64, 49, 50, 38, 120, 121; 424/61, 401; 252/182.13, 182.18, 182.22, 182.29

(56) References Cited

U.S. PATENT DOCUMENTS

| | | | |
|---|---|---|---|
| 2,979,061 A | 4/1961 | Greenman et al. ............ 132/73 |
| 3,629,187 A | 12/1971 | Waller ...................... 260/41 R |
| 3,709,866 A | 1/1973 | Waller ...................... 260/27 R |
| 3,928,113 A | 12/1975 | Rosenberg | |
| 4,089,763 A | 5/1978 | Dart et al. ............. 204/159.23 |
| 4,174,307 A | 11/1979 | Rowe .................... 204/159.19 |
| 4,189,365 A | 2/1980 | Schmitt et al. ........ 204/159.23 |
| 4,229,431 A | 10/1980 | Lee, Jr. et al. ............... 424/61 |
| 4,260,701 A | 4/1981 | Lee, Jr. ...................... 525/303 |
| 4,596,260 A | 6/1986 | Giuliano ...................... 132/73 |
| 4,600,030 A | 7/1986 | Newman ................... 132/88.5 |
| 4,666,952 A | 5/1987 | Henne et al. ................. 522/14 |
| 4,682,612 A | 7/1987 | Giuliano ...................... 132/73 |
| 4,690,369 A | 9/1987 | Giuliano ...................... 249/55 |
| 4,704,303 A | 11/1987 | Cornell ..................... 427/53.1 |
| 4,718,957 A | 1/1988 | Sensenbrenner ........... 156/152 |
| 4,721,735 A | 1/1988 | Bennett et al. ............... 522/71 |
| 4,745,003 A | 5/1988 | Sirkoch et al. ............ 427/54.1 |
| 4,766,005 A | 8/1988 | Montgomery et al. ......... 427/4 |
| 4,813,875 A | 3/1989 | Hare ......................... 433/214 |
| 4,844,102 A | 7/1989 | Repensek et al. ............. 132/73 |
| 4,846,165 A | 7/1989 | Hare et al. .................. 128/156 |
| 4,863,993 A | 9/1989 | Montgomery ............... 524/854 |
| 4,867,680 A | 9/1989 | Hare et al. .................... 433/37 |
| 5,071,888 A | 12/1991 | Kubota ........................ 522/34 |
| 5,118,495 A | 6/1992 | Nafziger et al. .............. 424/61 |
| 5,177,120 A | 1/1993 | Hare et al. .................. 523/109 |
| 5,229,431 A | 7/1993 | Pinchuk ...................... 521/159 |
| 5,344,583 A * | 9/1994 | Bayless ...................... 510/118 |
| 5,407,666 A | 4/1995 | Patel et al. ................... 424/61 |
| 5,415,903 A | 5/1995 | Hoffman et al. ............. 428/15 |
| 5,453,451 A | 9/1995 | Sokol .......................... 522/42 |
| 5,456,905 A | 10/1995 | Valenty ....................... 424/61 |
| 5,516,509 A | 5/1996 | Marr-Leisy et al. .......... 424/61 |
| 5,637,292 A | 6/1997 | Thomas ....................... 424/61 |
| 5,662,891 A | 9/1997 | Martin ........................ 424/61 |
| 5,708,052 A | 1/1998 | Fischer et al. ............. 523/116 |
| 5,785,958 A | 7/1998 | Sirdesai et al. .............. 424/61 |
| 5,792,447 A | 8/1998 | Socci et al. .................. 424/61 |
| 5,824,373 A | 10/1998 | Biller et al. ................. 427/474 |
| 5,965,111 A | 10/1999 | Ellingson et al. ............ 424/61 |
| 5,985,951 A | 11/1999 | Cook .......................... 522/88 |
| 5,985,998 A | 11/1999 | Sommerfeld et al. | |

* cited by examiner

Primary Examiner—James J. Seidleck
Assistant Examiner—Sanza L. McClendon
(74) Attorney, Agent, or Firm—Deborah A. Peacock; Vidal A. Oaxaca; Peacock Myers & Adams, P.C.

(57) ABSTRACT

A composition for actinic radiation curable nail coatings and artificial nail tips comprising a BISGMA based urethane resin, an additional polymer, a photoinitiator, and having a viscosity of greater than approximately 80,000 cps. Composition may additionally comprise other additives known in the art and also methods of application of the composition alone and with related compositions.

53 Claims, No Drawings

RADIATION CURABLE NAIL COATINGS AND ARTIFICIAL NAIL TIPS AND METHODS OF USING SAME

CROSS-REFERENCE TO RELATED APPLICATIONS

This application is a continuation-in-part application of U.S. patent application Ser. No. 09/466,985, entitled "Pre-Bond Compounds For Radiation Curable Nail Coatings", to Pamela H. Lilley, filed on Dec. 17, 1999 ('985 application) now abandoned; U.S. patent application Ser. No. 09/466,986, entitled "Radiation Curable Nail Coatings", to Pamela H. Lilley, filed on Dec. 17, 1999 ('986 application) now U.S. Pat. No. 6,391,938; U.S. patent application Ser. No. 09/467,127, entitled "Finishing Compounds for Radiation Curable Nail Coatings", to Pamela H. Lilley, filed on Dec. 17, 1999 ('127 application) now U.S. Pat. No. 6,481,444; and U.S. patent application Ser. No. 09/912,816, entitled "Radiation Curable Nail Coatings", to Pamela H. Lilley, filed Jul. 24, 2001 ('816 application) now U.S. Pat. No. 6,599,908 which is a divisional of the '986 application. The specifications of these four patent applications are incorporated herein by reference.

BACKGROUND OF THE INVENTION

1. Field of the Invention (Technical Field)

The present invention relates to radiation curable nail treatment materials and methods of using the same. The invention is also applicable to treatment materials for keratin and proteinaceous surfaces on animals such as claws and hooves.

2. Background Art

Note that the following discussion refers to a number of publications by author(s) and year of publication, and that due to recent publication dates certain publications are not considered as prior art vis-à-vis the present invention. Discussion of such publications herein is given for more complete background and is not considered as an admission that such publications are prior art for patentability determination purposes.

Light curable nail coatings are disclosed in Billings, U.S. Pat. No. 5,194,292, entitled "Method of Drying and Bonding Nail Polish" ('292 patent); Cornell, U.S. Pat. No. 4,704,303, entitled "Nail Extension Composition" ('303 patent); and Guiliano, U.S. Pat. No. 4,682,612, entitled "Novel Process and Article for Preparing Artificial Nails" ('612 patent) which are incorporated herein by reference. The '292 patent describes a method of protecting common nail polish by applying a light curable clear coating over the polished nail.

The '303 patent discloses a coating composition based on an aliphatic or cycloaliphatic hydrocarbon urethane diacrylate or (meth)acrylate having a molecular weight of 250 to 500 and a viscosity of 5,000 to 30,000 cps. Radiation in the visible region is used to cure the coatings disclosed in the '303 patent.

The '612 patent discloses an organic solvent-free photocurable composition that has at least one liquid monomer in which an acrylated urethane oligomer is dissolved and crosslinked upon curing. Radiation in the ultraviolet (UV) region is used to cure the coatings disclosed in the '612 patent.

None of the prior art patents disclose the use of a Bisphenol A Diglycidyl Methacrylate ("BISGMA") based urethane resin or a polyether methacrylated urethane in combination with a BISGMA based urethane resin for radiation curable nail coatings. Further, the prior art patents do not disclose the use of a thiol in combination with the BISGMA based urethane resin to reduce photoinitiator levels for photopolymerization. Furthermore, these patents do not disclose the use of vinyl ether or maleimide functional materials alone or in combination with the BISGMA based urethane resin for nail coatings to reduce or eliminate photoinitiator levels for photopolymerization. Nor do any of these patents describe the use of radiation curable materials to produce tough, flexible artificial nail tips using thiol, vinyl ether or maleimide functional materials alone or in combination with BISGMA based urethane resin.

Traditional light curable coatings presently known in the art have a tendency to "run" during application, due to low viscosity. Consequently, coatings tend to impinge on the cuticle or other unwanted areas, and may also cause all or portions of the coating to disengage from the nail surface over time. A coating is needed which will not run or lift from the nail.

Another known problem with traditional light curable nail coatings is associated with the use of urethane resins in the coating formula. Often such urethane resins are made with high levels of toxic catalysts, potentially posing a significant risk of skin sensitization. Furthermore, traditional light curable nail coatings are often associated with the use of acrylates, which are known to pose a significantly higher risk of skin sensitization in the general population than methacrylates.

A further problem in known light curable nail coatings is "leftover" photoinitiator by-products formed by photopolymerization. These by-products can cause yellowing of the coating and risk skin sensitization in the general population. A coating is needed which comprises a reduced amount of photoinitiators to reduce yellowing and potentially harmful skin sensitization.

Finally, another problem with traditional light curable coatings is that, upon curing, the surface of the coating becomes sticky and rough due to an air-diffused layer, wherein the air inhibits curing. Generally, ethyl alcohol is applied to a coating surface to remove the undesirable air diffused layer. While effective, the alcohol is not preferred due to skin sensitivity.

Traditional nail coatings generally include two varieties: polish type, which cure by solvent evaporation, and polymer type, which cure by chemical reaction. If a wearer desires a more natural look, and has strong nails, a polish type material is usually chosen to enhance appearance and add protection. If a wearer has short, weak nails, and desires longer nail enhancements, then a polymer type material, used alone, or in conjunction with artificial nail tips, is suitable. Polymer type materials include, for example, powder/liquid systems and gel systems.

Gel systems, in contrast to the traditional polish and polymer-type systems particularly ultraviolet cured gel systems, often comprise a gel that is brushed onto the nails, cured, and shaped to create lifelike artificial nails. Gel systems are relatively easy to use, are applicable in less time, are lightweight on the nail, have no odor (or only minimal odor), are durable, and have a high quality shine. There is a real need in the art for gel systems that can be formulated to provide hard, semi-permanent and soft, removable radiation curable nail coatings (unlike the traditional systems). Gel coatings are needed which may be applied to provide a strong, durable, semi-permanent nail extension on which a clear (or colored) flexible, removable radiation-curable coating is subsequently applied and cured to give a dried coating in two minutes or less, in contrast to traditional nail polish drying by solvent evaporation (which takes from several minutes to hours for complete drying and a smudge-proof surface). Such gel coatings would give a more appealing and defect free appearance which is smudgeproof and may be applied on top of current traditional powder/liquid systems as an attractive alternative to nail polish.

Yet another problem with some currently available colored gel topcoatings is that they cannot be removed from semi-permanent nail extensions using simple foil/solvent soak-off procedures at rebalance time. Instead, they must be removed by hand or machine filing and in doing so remove some of the supporting structure beneath them. The nail technician must then recreate this supporting structure at rebalance time in addition to filling in the area of new growth. Therefore, there is a need for an easily removable gel top coating from a nail extension.

Some other clear and colored gel nail systems are removable from natural nails and can be used for extending a nail and topcoating a nail. These, however, do not provide for semi-permanent extensions of the nails with removable gel topcoatings. In these types of removable gel systems, the extension is removed from the nail at the same time the gel topcoating is removed with the foil/solvent method, causing the nail technician more time and effort to rebuild the extension before gel topcoating.

Overall, a need exists for a material, colored or not, which is easily applied, dries rapidly, does not yellow or cause skin sensitization in the general population, protects the nail more than polish, and can be removed when the wearer desires. Such a material is described in an embodiment of the present invention. In addition, for wearers of artificial nail enhancements, there is a need for a coating, which dries rapidly (almost immediately), doesn't chip, can be easily removed at a later date for versatility, leaving an intact surface which requires less filing for rebalance.

Current artificial nail tips are made from injection molded plastics, which are not entirely compatible with gel nail systems, resulting in delamination of the gel from the tip. Therefore, there is a need for a radiation curable artificial nail tip with good strength, flexibility like a natural nail, and excellent compatibility with gel systems, thereby reducing delamination of the coating from the tip and preventing softening and dissolution of the tips during the soak-off procedure.

The radiation curable coatings of various embodiments of the present invention, and aforementioned related disclosures, satisfy such a need. The inventive methods of embodiments of the present invention also help to address this need.

SUMMARY OF THE INVENTION (DISCLOSURE OF THE INEVENTION)

The radiation curable nail and/or artificial nail tip coating composition of the present invention comprises a composition comprising: a polymerizable compound preferably a BISGMA urethane resin; a photoinitiator; and, preferably an alternate polymer wherein the composition is of a sufficient viscosity to be applied to natural nails and artificial nail tips. Additionally, photoaccelerators, a coupling agent, and other additives disclosed in the embodiment herein may be incorporated.

In the preferred embodiment the composition optionally comprises at least one additive selected from the group of plasticizers, secondary photoinitiators or photosensitizers, colorants, dyes, inhibitors, oxygen scavengers, dispersion aids, waxes, fillers, nanofillers, organsols, fibers, and adhesion promoting materials. In the preferred embodiment the composition preferably optionally comprises at least one polymerizable (meth)acrylate resin and wherein the (meth)acrylate resin optionally comprises a (meth)acrylated urethane resin and wherein the photoinitiator optionally comprises at least one initiator selected from the group of phosphinates, phosphine oxides, sulfanyl ketones, sulfonyl azides, polymeric morpholinoketones, an alpha-amino from Ciba-Geigy known as CGI 113, and iodonium hexafluorophosphate salts. And, the photoaccelerator preferably optionally comprises at least one accelerator selected from the group of aliphatic amines and aromatic amines and wherein the organo-metallic coupling agent optionally comprises at least one coupling agent selected from the group of titanate coupling agents.

In an alternate embodiment, the radiation curable nail and/or artificial nail tip coating composition of the present invention comprises photopolymerizable resin blend preferably comprising a polymerizable BISGMA urethane resin; an additional polymer; and a photoinitiator. The composition is preferably of a sufficient viscosity to be applied to natural nails and artificial nail tips. The composition preferably but optionally comprises a coupling agent and/or at least one additive selected from the group of plasticizers, secondary photoinitiators or photosensitizers, photoaccelerators, colorants, dyes, inhibitors, oxygen scavengers, optical brighteners, dispersion aids, waxes, fillers, nanofillers, organsols, fibers, and adhesion promoting materials. The composition preferably optionally comprises at least one polymerizable (meth)acrylate resin, wherein the (meth)acrylate resin preferably comprises a (meth)acrylated urethane resin. Preferably at least one initiator is selected from the group of phosphinates, phosphine oxides, sulfanyl ketones, sulfonyl azides, polymeric morpholinoketones, an alpha-amino from Ciba-Geigy known as CGI 113, and iodonium hexafluorophosphate salts. The photoaccelerator of the composition optionally comprises at least one accelerator selected from the group of aliphatic amines and aromatic amines.

In yet another embodiment, the radiation curable nail and/or artificial nail tip coating composition of the present invention comprises a photopolymerizable resin blend comprising a polymerizable BISGMA urethane resin, a polyol modified (meth)acrylated urethane, and a photoinitiator. The composition should have a sufficient viscosity to be applied to natural nails and artificial nail tips. The composition optionally comprises a coupling agent and/or at least one additive selected from the group of plasticizers, secondary photoinitiators or photosensitizers, photoaccelerators, colorants, dyes, inhibitors, oxygen scavengers, optical brighteners, dispersion aids, waxes, fillers, nanofillers, organsols, fibers, and adhesion promoting materials. The composition optionally comprises at least one polymerizable (meth)acrylate resin, wherein the (meth)acrylate resin preferably comprises a (meth)acrylated urethane resin. The photoinitiator optionally comprises at least one initiator selected from the group of phosphinates, phosphine oxides, sulfanyl ketones, sulfonyl azides, polymeric morpholinoketones, an alpha-amino from Ciba-Geigy known as CGI 113, and iodonium hexafluorophosphate salts. The photoaccelerator optionally comprises at least one accelerator selected from the group of aliphatic amines and aromatic amines.

In still another embodiment, the radiation curable nail and/or artificial nail tip coating composition of the present invention comprises from approximately 20–99% of a polymerizable BISGMA urethane resin, and a photoinitiator. The composition is strong and durable after curing, and contains a substantial proportion of photopolymerizable resin blend of a sufficient viscosity to be applied to natural nails and artificial nail tips. The composition optionally comprises a coupling agent and/or at least one additive selected from the group of plasticizers, secondary photoinitiators or photosensitizers, photoaccelerators, colorants, dyes, inhibitors, oxygen scavengers, optical brighteners, dispersion aids, waxes, fillers, nanofillers, organsols, fibers, and adhesion promoting materials. The composition optionally comprises at least one polymerizable (meth)acrylate resin, wherein the (meth)acrylate resin preferably comprises a (meth)acrylated urethane resin. The photoinitiator optionally comprises at least one initiator selected from the group of phosphinates, phosphine oxides, sulfanyl ketones, sulfonyl azides, polymeric morpholinoketones, an alpha-amino from Ciba-Geigy known as CGI 113, and iodonium hexafluorophosphate salts. The photoaccelerator optionally comprises at least one accelerator selected from the group of aliphatic amines and aromatic amines.

In yet another embodiment, the radiation curable nail and/or artificial nail tip coating composition of the present invention comprises from approximately 1% to approximately 30% of a polymerizable BISGMA urethane resin, from approximately 1% to approximately 99% of a polyol modified (meth)acrylated urethane, and a photoinitiator. The composition is softenable and removable from the nail by polar solvents, and is of a sufficient viscosity to be applied to natural nails and artificial nail tips. The composition optionally comprises a coupling agent and/or at least one additive selected from the group of plasticizers, secondary photoinitiators or photosensitizers, photoaccelerators, colorants, dyes, inhibitors, oxygen scavengers, dispersion aids, waxes, fillers, nanofillers, organsols, optical brighteners, fibers, and adhesion promoting materials. The composition optionally comprises at least one polymerizable (meth)acrylate resin, wherein the (meth)acrylate resin preferably comprises a (meth)acrylated urethane resin. The photoinitiator optionally comprises at least one initiator selected from the group of phosphinates, phosphine oxides, sulfanyl ketones, sulfonyl azides, polymeric morpholinoketones, an alpha-amino from Ciba-Geigy known as CGI 113, and iodonium hexafluorophosphate salts. The photoaccelerator optionally comprises at least one accelerator selected from the group of aliphatic amines and aromatic amines.

In another embodiment, the present invention comprises a method for increasing the soak-off characteristics and susceptibility to polar solvents of the nail coating composition. The method comprises the steps of providing a nail coating composition and adding a polymerizable polyol modified (meth)acrylate urethane resin to the composition. The composition optionally comprises a polymerizable BISGMA urethane resin.

In yet another embodiment, the present invention comprises a method of applying a soak-off nail coating composition to a coated nail. The method comprises the steps of preparing and providing a coated extended nail; applying a composition comprising a radiation curable gel coating (which is softenable and removable with polar solvents); and curing the applied composition. The radiation curable gel coating may comprise a polyol modified (meth)acrylate resin or a (meth)acrylate urethane resin.

In another embodiment, the present invention comprises a method of preparing and applying a soak-off nail coating for a natural nail or a coated nail. The method comprises the steps of mixing a clear soak-off UV curing gel composition with standard nail polish to provide a colored UV curing soak-off gel composition; applying the prepared UV gel/polish mixture to the natural or coated nail; and curing the composition. Predetermined ratios may be utilized in the mixing step.

In yet another embodiment, the present invention comprises a method of removing a soak-off nail coating composition from a coated nail. The method comprises the steps of providing a nail coated with a radiation cured composition, wherein the cured composition may comprise a polyol modified (meth)acrylate polymer or a (meth)acrylate urethane resin; and soaking the coated nail with a solvent, wherein the solvent may comprise a polar solvent.

In another embodiment, the present invention comprises a method of removing a soak-off nail coating composition from a coated nail. The method comprises the steps of providing a nail coated with a radiation cured composition, wherein the cured composition may comprise a polyol modified (meth)acrylated urethane, a BISGMA urethane, and a photoinitiator, and soaking the coated nail with a solvent. The solvent may comprise a solvent which may be a polar solvent.

In a further embodiment, the radiation curable nail coatings or artificial nail tip coating compositions of the present invention comprise a polymerizable (meth)acrylate resin; functional materials selected from thiol, vinyl ether, cycloaliphatic epoxide, and maleimide functional materials; and a photoinitiator. The composition is of a sufficient viscosity to be applied to natural nails and artificial nail tips. The composition optionally comprises a coupling agent and/or at least one additive selected from the group of plasticizers, secondary photoinitiators or photosensitizers, photoaccelerators, colorants, dyes, inhibitors, oxygen scavengers, dispersion aids, waxes, fillers, nanofillers, organsols, optical brighteners, fibers, and adhesion promoting materials. The composition optionally comprises a (meth)acrylated urethane resin. The photoinitiator optionally comprises at least one initiator selected from the group of phosphinates, phosphine oxides, sulfanyl ketones, sulfonyl azides, polymeric morpholinoketones, an alpha-amino from Ciba-Geigy known as CGI 113, and iodonium hexafluorophosphate salts.

In yet another embodiment, the radiation curable nail coatings or artificial nail tip coating compositions of the present invention comprise a polymerizable BISGMA urethane resin; functional materials of thiol, vinyl ether, cycloaliphatic epoxide, or maleimide functionality; and a photoinitiator. The composition is of a sufficient viscosity to be applied to natural nails and artificial nail tips. The composition optionally comprises a coupling agent and/or at least one additive selected from the group of plasticizers, secondary photoinitiators or photosensitizers, photoaccelerators, colorants, dyes, inhibitors, oxygen scavengers, optical brighteners, dispersion aids, waxes, fillers, nanofillers, organsols, fibers, and adhesion promoting materials. The composition optionally comprises at least one polymerizable polyol modified (meth)acrylate urethane resin. The photoinitiator optionally comprises at least one initiator selected from the group of phosphinates, phosphine oxides, sulfanyl ketones, sulfonyl azides, polymeric morpholinoketones, an alpha-amino from Ciba-Geigy known as CGI 113, and iodonium hexafluorophosphate salts.

In another embodiment, the radiation curable nail coatings or artificial nail tip coating compositions of the present invention comprise a composition comprising maleimide, cycloaliphatic epoxide and/or vinyl ether functionality in combination with a polymerizable resin and a photoinitiator. The composition is of a sufficient viscosity to be applied to natural nails and artificial nail tips. The composition optionally comprises a coupling agent and/or at least one additive selected from the group of plasticizers, photosensitizers, colorants, dyes, inhibitors, oxygen scavengers, optical brighteners, dispersion aids, waxes, fillers, nanofillers, organsols, fibers, and adhesion promoting materials.

In another embodiment, the radiation curable composition of the present invention comprises a thiol, maleimide, vinyl ether, cycloaliphatic epoxide, and/or (meth)acrylate functionality used alone or in combination along with photoinitiators, photosensitizers, photoaccelerators, coupling agents, plasticizers, inhibitors, oxygen scavengers, optical brighteners, colorants, dyes, dispersion aids, waxes, fillers, nanofillers, organosols, fibers, and adhesion promoting monomers or polymers to prepare pre-formed artificial nail tips for use with radiation curable gel nail coatings.

A primary object of the present invention is to provide hard and durable coatings for the cosmetic industry, particularly for the cosmetic nail industry.

A further object of the invention is to provide soft, flexible, and removable natural nail coatings for the cosmetic industry, particularly the cosmetic nail industry.

A further object of the invention is to provide soft, flexible, and removable coatings, which can be applied to nail enhancements and removed at a later date for versatility, without destroying the underlying structure and reducing the filing necessary at rebalancing time.

A further object of the invention is to provide pre-formed nail tips that will not readily delaminate from radiation curable coatings.

A primary advantage of the present invention is that the coating materials are of a sufficient viscosity and/or other Theological properties such that the materials do not tend to run into the cuticle or off the nail and onto the finger or toe, etc. or soak-off during common foil/solvent soak-off procedures.

Another advantage of the present invention is that the coating materials exhibit a low degree of skin sensitivity.

A further advantage of the present invention is that the coating materials do not cause a burning sensation in a user during the curing process.

Yet another advantage of the present invention is that the coating materials create less dust in the filing stage of forming the artificial nail.

Another advantage of the present invention is that the coating materials of the present invention require reduced or eliminated levels of photoinitiators.

Another advantage of the present invention is that coating materials cure to a more tack-free surface, resulting in higher gloss.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENTS

Best Modes for Carring Out the Invention

The present invention comprises a variety of radiation curable materials for treating nails. The present invention also comprises a variety of methods for applying these materials. Related methods and compositions are set forth in U.S. patent application Ser. No. 09/466,985, entitled "Pre-Bond Compounds For Radiation Curable Nail Coatings"; U.S. patent application Ser. No. 09/466,986, entitled "Radiation Curable Nail Coatings"; U.S. patent application Ser. No. 09/467,127, entitled "Finishing Compounds for Radiation Curable Nail Coatings"; and U.S. patent application Ser. No. 09/912,816, entitled "Radiation Curable Nail Coatings," which are incorporated herein by reference.

The stiffness, durability, and toughness of radiation curable nail coatings, in their cured state, varies depending on polymer composition and polymerization initiation. The present invention recognizes that heat generation during curing, coating gloss, nature of the cured surface, and removability also relate to the polymer composition, formulation additives, and the particular photoinitiator system used. Formulas of the present invention allow for a wide range of radiation curable nail coating materials that meet the heat requirements, stiffness, durability, toughness, gloss, and removal needs of most all wearers of artificial nail products. Some of the materials of the present invention are optionally sculptable to form an artificial nail and, once applied, are preferably removable through filing rather than through soaking. Alternatively, other materials of the present invention are preferably removable through soaking rather than through filing.

Pre-formed artificial nail tips are typically made from injection molded plastics, e.g., ABS, nylon and acetate. They are typically applied to the fingernail through the use of cyanoacrylate glue. They then must be filed to blend into the fingernail and to roughen the surface for the application of the nail coating. Certain compositions of the present invention illustrate that a stronger bond results from the application of a radiation curable gel coating to a radiation curable pre-formed artificial nail tip.

In various embodiments of the present invention, the radiation curable compositions are based on photochemistry described below and in aforementioned related applications. For example, in various embodiments, compositions or materials of the present invention may comprise a photochemical system of phosphinate, amine functional compound, neoalkoxytitanate, and/or a secondary photoinitiator. Throughout this disclosure, the term "material," in singular and/or plural may substitute for composition, e.g., composition of matter.

While the compositions of the present invention can include acrylates, methacrylates are preferred because methacrylates are less likely to cause skin sensitization than acrylate formulas. The term "(meth)acrylate" as used herein, means methacrylate, acrylate, or mixtures thereof.

Ranges for BISGMA urethane resin and (meth)acrylated polyether urethane disclosed herein and in prior, related patent applications are, in some embodiments, suitable for a supporting material that serves to semi-permanently extend a nail. Once applied, such a material is removed by filing rather than by soaking off in a solvent, such as, acetone.

Soak-off materials of the present invention comprise resins with or without the use of additives. The term "soak-off" refers to the ability to remove a material from a nail with a solvent-based solution, typically in conjunction with a "wrap," for example, but not limited to, an aluminum foil wrap. According to the present invention, it is possible to tailor the characteristics of a soak-off material by varying resin type and resin concentration.

In the present invention, the concentration of (meth) acrylated polyether urethane resin in a soak-off material may be higher than in a comparable semi-permanent, non soak-off material. The concentration of BISGMA urethane resin in a soak-off material may be lower than in semi-permanent, non soak-off material. A permanent type resin may be altered through the use of (meth)acrylated polyether urethane resins to give desirable soak-off characteristics. According to the present invention, adjustable parameters include, but are not limited to, (i) blend ratio of BISGMA urethane resin to (meth)acrylated polyether urethane and (ii) molecular weight of (meth)acrylated polyether urethane, which optionally comprise blends of different molecular weight (meth)acrylated polyether urethanes. In the present invention, both semi-permanent and soak-off coating compositions may be altered through the use of thiol, maleimide, or vinyl ether functional materials to reduce photoinitiator levels in the compositions, improve the surface curing, and further decreasing the chance for skin sensitization. In alternate embodiments, pre-formed artificial nail tips are prepared using combinations of any of radiation curable (meth)acrylate, thiol, maleimide, cycloaliphatic epoxide, or vinyl ether functional materials to compliment the radiation curable nail coatings and prevent delamination and remain intact during the soak-off procedure. A key point of the radiation cured artificial nail tips is that they cannot be soaked off. This is particularly important when using the soak-off color on top of a non soak-off system. Currently, these soak-off colors cannot be used with a person who has artificial nail tips because they soften in the foil soak-off process.

An alternative method to gluing the radiation cured artificial nail tips on the nail is to use the gel nail coating itself to bond the artificial nail tips onto the natural nail. Therefore, the artificial nail tip is even less likely to delaminate from the coating and the natural nail in normal use, particularly during the foil/solvent soak-off procedure.

In the embodiments of the present invention, soak-off materials give rise to a new option for wearers who desire: 1) chip-proof color on their natural nails; 2) protection for new growth; 3) rapid drying to a smudgeproof surface; and/or 4) versatility to easily change color. Furthermore, in a variety of embodiments, soak-off materials used in conjunction with semi-permanent materials give rise to a new option for nail technicians who desire: 1) chip-proof color for their clients; 2) easy color removal at rebalance time; 3) less filing at rebalance; and 4) rapid drying to a smudgeproof surface.

Pre-Bond Materials of the '985 Application

The following examples are disclosed in the '985 application, which is hereby incorporated by reference. The pre-bond material comprises at least one solvent, hydrogenated rosin, and a (meth)acrylate oligomer. Solvents include, but are not limited to, alcohols, ketones, and esters are useful in the pre-bond composition. Useful hydrogenated rosins include, but are not limited to, Foral 85 and Endere™ S from Hercules. The (meth)acrylate oligomers Sarbox 500E50 and Sarbox 600 from Sartomer have been found to be particularly useful with their acid functionality. A preferred composition preferably contains from approximately 50% to approximately 80% solvent, from approximately 10% to approximately 20% hydrogenated rosin, and from approximately 10% to approximately 20% (meth)acrylate oligomer.

In actual use, the nail is prepared for the radiation curable nail coating and a thin layer of the pre-bond material is applied. The solvent is allowed to air dry for approximately one minute or as necessary. A tacky surface results to which the radiation curable coating is then applied. More specific procedures will be detailed regarding the application of the radiation curable coating in the examples.

Radiation Curable Nail Coating Materials of the '986 Application

The following embodiments are disclosed in the '986 application, which is hereby incorporated by reference. The present invention also similarly comprises inventive compositions for application to, for example, natural nails, and artificial nail tips. The '986 application discloses a composition comprising a polymerizable resin material, a photoinitiator, and a photoaccelerator.

In a preferred embodiment, the composition comprises between approximately 30 and approximately 98 percent by weight, preferably between approximately 60 and approximately 95 percent by weight of polymerizable resin material; between approximately 0.05 and approximately 10 percent by weight, preferably between approximately 0.1 and approximately 5 percent by weight of photoinitiator; and between approximately 0.1 and approximately 5 percent by weight, preferably between approximately 0.25 and approximately 1 percent by weight of photoaccelerator. In other embodiments, the polymeric material or materials comprises, for example only, (meth)acrylates, and the photoinitiator comprises for example only phosphinates, phosphine oxides and/or sulfanyl ketones (e.g., Esacure™ 1001). in further embodiments, the photoaccelerator comprises aliphatic amines and/or aromatic amines, preferably ethyl 4-dimethylaminobenzoate, butoxyethyldimethylaminobenzoate, octyl-para-dimethylaminobenzoate, and/or dimethylaminoethyl (meth)acrylate.

In another embodiment of the '986 application, the inventive compositions optionally comprise a coupling agent. Compositions comprising between approximately 0.01 and approximately 0.5 percent by weight and preferably between approximately 0.05 and approximately 0.15 percent by weight of a coupling agent are within the scope of the present invention. In one embodiment, the coupling agent comprises an organo-metallic, preferably an organo-titanate coupling agent such as isopropyldimethylacrylisosteroyl titanate, tetraisopropyl(dioctyl)phosphito titanate, neopentyl (diallyl)oxy, tri(dodecyl)-benzene-sulfonyl titanate, and/or neopentyl(diallyl)oxy, trineodecanonyl titanate.

In further embodiments of the '986 application, the composition optionally comprise at least one additive such as, but not limited to, plasticizers, secondary photoinitiators, colorants, dyes, inhibitors, fillers, fibers, and/or adhesion promoting polymers. The composition may comprise between approximately 0 and approximately 50 percent by weight, preferably between approximately 1 and approximately 20 percent by weight of additive. The inventive compositions optionally comprise a plasticizer (such as, but not limited to, phthalates, adipates, and/or sulfonamides), a secondary photoinitiator (such as, but not limited to, camphorquinone, benzildimethylketal, and or benzophenone), a colorant (such as, but not limited to, barium, calcium, or aluminum lakes, iron oxides, talcs, carmine, titanium dioxide, chromium hydroxides, ferric ferrocyanide, ultramarines, titanium dioxide coated mica platelets, and/or bismuth oxychlorides), and an inhibitor (such as, but not limited to, hydroquinone, methyl ether hydroquinone and/or butylated hydroxy toluene), a filler (such as, but not limited to, mineral fillers and/or polymeric fillers), fibers, and an adhesion promoting polymer (such as, but not limited to, methacryloyloxy-ethyl-phthalate).

In another embodiment the inventive composition of the '986 application comprises a BISGMA urethane resin, a polyether, (meth)acrylated urethane resin, a photoinitiator, and a plasticizer. In one embodiment, the composition comprises: between approximately 30 and approximately 90 percent by weight, preferably between approximately 5 and approximately 70 percent by weight, of a BISGMA urethane resin; between approximately 0.5 and approximately 50 percent by weight, preferably between approximately 10 and approximately 40 percent by weight, of (meth)acrylated urethane resin; between approximately 0.05 and approximately 10 percent by weight, preferably between approximately 0.25 and approximately 5 percent by weight, of photoinitiator; and between approximately 0.1 and approximately 5 percent by weight, preferably between approximately 0.25 and approximately 1 percent by weight, of photoaccelerator. In another embodiment, the composition comprises a (meth)acrylated urethane resin having a viscosity greater than 100,000 cps; a photoinitiator (such as, but not limited to, camphorquinone, ethyl 2,4,6-trimethylbenzoyldiphenyl phosphine oxide, benzildimethylketal, and/or benzophenone); and a photoaccelerator (such as, but not limited to, aliphatic amines and/or aromatic amines, preferably ethyl 4-dimethylaminobenzoate, butoxyethyl dimethylaminobenzoate, octyl-para-dimethylaminobenzoate, and/or dimethylamino ethyl methacrylate).

In yet another embodiment, inventive compositions optionally comprise a coupling agent, for example but not limited to, between approximately 0.01 and approximately 0.5 percent by weight and preferably between 0.05 and approximately 0.15 percent by weight of a coupling agent. In one embodiment, the coupling agent comprises an organo-metallic, preferably an organo-titanate coupling agent (such as, but not limited to, isopropyldimethylacrylisosteroyl titanate, tetraisopropyl(dioctyl)phosphito titanate, neopentyl (diallyl)oxy, tri(dodecyl)-benzene-sulfonyl titanate, and/or neopentyl(diallyl)oxy, trineodecanonyl titanate).

Finally, inventive compositions of the '986 application optionally comprise at least one additive such as plasticizers, secondary photoinitiators, colorants, dyes, inhibitors, fillers, fibers, and/or adhesion promoting polymers. In one embodiment, a composition comprises between approximately 0 and approximately 50 percent by weight, preferably between approximately and approximately 20 percent by weight, of additive. In another embodiment, an inventive composition optionally comprises a plasticizer (such as, but not limited to, phthalates, adipates, and/or sulfonamides); a secondary photoinitiator (such as, but not limited to, camphorquinone, benzildimethylketal, and/or benzophenone); a colorant (such as, but not limited to, barium, calcium, or aluminum lakes, iron oxids, talcs, carmine, titanium dioxide, chromium hydroxides, ferric ferrocyanide, ultramarines, titanium dioxide coated mica platelets, and/or bismuth oxychlorides); and inhibitor (such as, but not limited to, hydroquinone, methyl ether hydroquinone and/or butylated hydroxy toluene); a filler (such as, but not limited to, mineral fillers and/or polymeric fillers); fibers; and an adhesion promoting polymer (such as, but not limited to, methacryloyloxy ethyl phthalate).

Finishing Material of the '127 Application

The following embodiments are disclosed in the '127 application, which is hereby incorporated by reference. The present invention further comprises a "finishing" material for application to cured polymeric and/or urethane nail coatings. In one embodiment the finishing material comprises at least one solvent and natural oil (e.g., animal and/or vegetable oil). In such an embodiment, for example, the natural oil comprises castor oil. In one embodiment the finishing material comprises: between approximately 50 and approximately 80 percent by weight, of solvent; and between approximately 5 and approximately 40 percent by weight, preferably between approximately 10 and approximately 30 percent by weight, of natural oil. In yet another embodiment, the finishing material optionally comprises a solvent (such as, but not limited to, acetone, ethyl alcohol, ethyl acetate, isopropyl alcohol, and/or methyl ethyl ketone); and a vegetable oil (such as, but not limited to, castor oil). Further, the material optionally comprises at least one fragrance material (such as, but not limited to, lavender oil).

The present invention comprises a method to enhance the polished characteristics of a coated nail or nail tip. In one embodiment, the method comprises the steps of: applying a material comprising at least one solvent and a vegetable oil to the coated natural nail or nail tip; and cleaning the coated natural nail or nail tip, preferably with a clean cloth or cotton. The applied material optionally comprises between approximately 30 and approximately 90 percent by weight of solvent (such as, but not limited to, acetone, ethyl alcohol, ethyl acetate, isopropyl alcohol, and methyl ethyl ketone), and between approximately 5 and approximately 40 percent by weight of vegetable oil (such as, but not limited to, castor oil). The applied material optionally comprises a fragrant material (such as, but not limited to, lavender oil).

In an additional embodiment, the method comprises the steps of: applying a material comprising at least one solvent, a vegetable oil, and a lanolin material to the coated nail or nail tip; and cleaning the coated nail or nail tip with a clean cloth or cotton. The applied material optionally comprises between approximately 30 and approximately 90 percent by weight of solvent (such as, but not limited to, acetone, ethyl alcohol, ethyl acetate, isopropyl alcohol, and methyl ethyl ketone), between approximately 5 and approximately 40 percent by weight of vegetable oil (such as, but not limited to, castor oil), and between approximately 5 and approximately 30 percent by weight of a lanolin material (such as, but not limited to, PEG-75 lanolin, hydroxylated lanolin and/or hydrogenated lanolin). The applied material optionally comprises a fragrant material (such as, but not limited to, lavender oil).

Radiation Curable Coating Composition Methods of the Present Invention

The present invention relates to using actinic (e.g., visible and UV) radiation curable compositions to coat artificial nail tips, to extend, strengthen, and coat natural nails, and to prepare pre-formed artificial nail tips for use with radiation curable nail coatings. (Electron beam (EB) or other light beam curable materials are also within the scope of the present invention.) The coating materials are applied to the natural nail or alternatively to the natural nail and a pre-formed nail tip attached to the natural nail (regardless of whether the tip is an injected molded type or a radiation cured type). The compositions of the present invention are capable of reacting with actinic radiation, even when highly colored. The compositions can be formulated in clear, opaque white, translucent and opaque colors. The composition may cure, in preferred embodiments, in less than approximately two minutes with actinic radiation.

The compositions of the present invention are polymeric, wherein the term "polymeric" or "polymeric materials" as used throughout the specification and claims is intended to include resins, monomers, oligomers, and polymers. For example, a resin (natural and/or synthetic) is a polymeric material. The term "resin" as used throughout the specification and claims, also generally includes "oligomers," which are typically molecules having a relatively intermediate molecular mass.

In use on a natural nail, a biocompatible solvent-based adhesive resin (pre-bond material) is preferably used to enhance the bond between the radiation curable nail coatings and the natural nail. The natural nails are typically prepared by filing, and then applying a thin coat of the solvent-based adhesive resin (which evaporates to leave a "sticky" layer) to the surface of the natural nail, typically beginning at the cuticle area. The radiation curable nail coating is then applied to the adhesive.

Another method incorporates pre-formed artificial nail tips (injected molded type or radiation cured type). The artificial nail tip is attached to the natural nail, as is known in the art. A thin coat of the solvent based-adhesive resin is preferably applied to the surface of the natural nail typically beginning at the cuticle area and ending at the surface of the nail tip. The radiation curable coating is then applied to the sticky adhesive on the surface of the natural nail as well as to the nail tip. The use of the adhesive resin enhancer in both methods would prevent lifting of the cured coating from the natural nail, adding longevity and enhancing appearance. The pre-bond materials illustrated in examples 1, 2, and 2A below are useful to the methods of the present invention:

TABLE 1

Pre-Bond Examples 1, 2, 2A (quantities in grams)

| Ingredient | 1 | 2 | 3 |
| --- | --- | --- | --- |
| Acetone | 8.52 | 52.43 | 14.0 |
| Sarbox 500E50 | 1.52 | 11.18 | — |
| Sarbox 600 | — | — | 3.0 |
| Foral 85 | — | 11.33 | 3.0 |

Coating Materials of the Present Invention

The present invention relates to actinic radiation, preferably UV radiation, curable materials used to coat natural nails and pre-formed artificial nail tips (an injected molded type or radiation cured type). In the preferred embodiment, the coating materials comprise (a) polymerizable BISGMA urethane resin; (b) a polyol modified (meth)acrylated urethane; and (c) a photoinitiator, preferably a phosphinate, phoshine oxide, sulfanyl ketone, sulfonyl azide, polymeric morpholinoketone, an alpha-amino ketone (e.g., CGI 113, from Ciba-Geigy), or iodonium hexafluorophosphate salt. The coating materials may further comprise a coupling agent, preferably, a titanate coupling agent, and various other additives such as plasticizers, secondary photoinitiators, photoaccelerators, colorants, dyes, inhibitors, oxygen scavengers, optical brighteners, dispersion aids, waxes, fillers, nanofillers, organsols, fibers, and adhesion promoting monomers or polymers, or other additives known in the art.

The preferred BISGMA based urethane resins are formed from the reaction product of BISGMA with trimethylhexamethylene diisocyanate or isophorone diisocyanate. However, other alkyl isocyanates wherein the alkyl group ranges from $C_1$ to $C_{18}$, aryl isocyanates (e.g., phenyl and naphthyl isocyanates and optionally substituted by one or more alkyl or other non-reactive group, and cycloalkyl isocyanates, as well as diisocyanates or polyisocyanates including the alkylene diisocyanates wherein the alkylene group ranges from $C_2$ to about $C_{18}$ and arylene and substituted arylene di- and polyisocyanates are suitable.

BISGMA based urethane resin is preferably prepared by reacting the hydroxyl functions of BISGMA with a hydrocarbon diisocyanate. For example, BISGMA may be diluted with di(meth)acrylate monomers, followed by catalyst addition and then the diisocyanate addition. The reaction mixture is then heated (approximately 55° C.) until essentially all the diisocyanate has reacted to the BISGMA urethane. (BISGMA can be purchased from Esstech, and is sold as Nupol 46-4005 from Cook Composites and Polymers.) The final urethane resin comprises between approximately 30 and approximately 70 percent by weight of the di(meth) acrylate monomers based on the total weight of the composition. Di(meth)acrylate monomers are well suited for the dilution step because they exhibit relatively low volatility and odor and serve as crosslinking agents in the urethane resin. Examples of suitable di(meth)acrylate monomers include but are not limited to diethylene glycol di(meth) acrylate, 1,6-hexanediol di(meth)acrylate, triethylene glycol di(meth)acrylate, ethoxylated bisphenol A di(meth)acrylate, polyethylene glycol di(meth)acrylate, and 1,4-butanediol di(meth)acrylate.

Any urethane catalyst known in the art may serve as a catalyst for the present invention for preparing the BISGMA polymer. Pre-prepared polymer may be utilized instead of utilizing the modification steps discussed herein. However, preferred urethane catalysts include, but are not limited to, tin compounds (such as dibutyl tin dilaureate and stannous octoate). The catalysts are preferably used at levels between approximately 0.005 and approximately 0.10 percent by weight in the urethane resin. The catalyst is added to the mixture of BISGMA and di(meth)acrylate monomers and mixed. A diisocyanate (e.g., aliphatic or cycloaliphatic hydrocarbon diisocyanate such as heptyl diisocyanate, trimethylhexamethylene diisocyanate, or isophorone diisocyanate) is added at levels between approximately 5% and approximately 12% by weight of the urethane resin. Alternatively, the diisocyanate may be diluted with di(meth) acrylate monomer to control the exothermic reaction. Once the urethane reaction is completed, a small amount of inhibitor, preferably butylated hydroxy-toluene, is added in an amount of between approximately 0.01 and approximately 0.10 percent by weight. The BISGMA resin is then allowed to cool.

The polyol modified (meth)acrylated urethane resin is added (using heat of 50–60° C., if necessary for thorough mixing). Once this resin blend is mixed, the other ingredients such as photoinitiators, plasticizers, secondary photoinitiators, photoaccelerators, oxygen scavengers, inhibitors, colorants, dyes, dispersion aids, waxes, fillers, nanofillers, organosols, fibers, and adhesion promoting monomers or polymers known in the art are added and mixed.

In alternate embodiments thiol, maleimide, cycloaliphatic epoxide, or vinyl ether functional materials are added to the BISGMA urethane resin to reduce photoinitiator levels, increase adhesion, flexibility and toughness, and improve surface-curing of nail coatings. Thiol functional materials, include but at not limited to, Trimethyolpropane tris(3-mercaptopropionate) from Evans Chemetics and Tris (3-mercaptopropionate) triethyl-1,3,5-triazine-2,4,6-(1H, 3H,5H)-trione. Maleimide functional materials include, but are not limited to, hydroxy ethylmaleimide, triethylene glycol biscarbonate bisethylmaleimide, 2-isopropyl urethane ethylmaleimide, 2-acryloyl ethylmaleimide, acetoxy ethyl maleimide, isophorone bisurethane bisethylmaleimide, N,N'-hexamethylenebismaleimide, and N,N'-(2,2,4-trimethylhexamethylene)-bismaleimide, and cycloaliphatic epoxides (e.g., Cyracure™ UVR series from Dow Chemicals), vinyl ether functional materials (e.g., Vectomer® Vinyl Ether monomers and oligomers specifically vectomer monomers such as 4010 (1,3-Benzenedicarboxylic acid, bis{4-(ethenyloxy)butyl}ester), 4060 (hexanedioic acid, bis{4-(ethenyloxy) butyl}ester), and 5015 (1,2,4-Benzenetricarboxylic acid, tris {4-(ethenyloxy) butyl}ester), VEctomer® oligomer 1312).

A combination of any of these (meth)acrylate, thiol, maleimide, cycloaliphatic epoxide or vinyl ether functional materials may also be useful to prepare the radiation cured pre-formed artificial nail tips of the present invention along with photoinitiators, photosensitizers, photoaccelerators, coupling agents, plasticizers, inhibitors, oxygen scavengers, optical brighteners, colorants, dyes, dispersion aids, waxes, fillers, nanofillers, organosols, fibers, and adhesion promoting monomers or polymers.

In the preferred embodiment, the material preferably comprises: 1) between approximately 20 and approximately 99 percent by weight and preferably between approximately 30 and approximately 70 percent by weight of component (A); 2) between approximately 10 and approximately 60 percent by weight and preferably between approximately 20 and approximately 50 percent by weight of component (B); and 3) between approximately 0.05 and approximately 10 percent by weight and preferably between approximately 0.10 and approximately 5 percent by weight of component (C). Alternate embodiments may further comprise between approximately 0.01 and approximately 0.5 percent by weight and preferably between approximately 0.05 and approximately 0.15 percent by weight of a coupling agent (component (D)); and between approximately 0 and approximately 50 percent by weight and preferably between approximately 1 and approximately 20 percent by weight of other additives (component or components (E)).

Component (A) comprises a polymerizable BISGMA urethane resin preferably prepared from an adduct of BISGMA and an aliphatic or cycloaliphatic hydrocarbon diisocyanate. Component (B) is preferably an aliphatic (meth) acrylated urethane (optionally polyol modified, e.g., polyether, polyester, polybutadiene, and/or polycarbonate) with a preferred viscosity greater than approximately 80,000 cps. Component (C) preferably comprises an acyl phosphine oxide (such as, but not limited to, 2,4,6-trimethylbenzoyldiphenylphosphine oxide) or a phosphinate (such as, but not limited to, ethyl 2,4,6-trimethylbenzoylphenylphosphinate, commonly available from BASF). Component (C) preferably comprises a photoinitiator (such as, but not limited to, a sulfanyl ketone, e.g., 1-{4-(4-benzoylphenylsulfanyl)phenyl}-2-methyl-2-(4-methylphenylsulfanyl) propan-1-one, available as Esacure™ 1001 from Lamberti spa in Italy or a sulfanyl azide, e.g., phenyl sulfonyl azide or naphthyl sulfonyl azide, or a polymeric morpholinoketone, e.g., Chivacure 3842, from Chitec Chemical, or an alpha-amino ketone e.g., CGI 113, from Ciba-Geigy, or an iodonium hexafluorophosphate salt, e.g., Photoinitiator 2076, from Rhodia). The preferred coupling agent, component (D), is an organic titanate coupling agent, such as but not limited to the monoalkoxy, chelate, quaternary, coordinate, cycloheteroatom or neoalkoxy titanates (available from Kenrich Petrochemicals). Additional and optional additives, component (E), may include plasticizers (e.g., the phthalates, adipates, citrates, butyl glycolates, and sulfonamides), other photoinitiators or photosensitizers (e.g., camphorquinone, benzildimethylketal, benzoyl biphenyl, 2,2-diethoxy acetophenone, 1-hydroxycyclohexylphenyl ketone, isopropylthioxanthone, 1-chloro-4-propoxythioxanthone, rose bengal, and benzophenone), photoaccelerators (e.g., aliphatic and aromatic amines), oxygen scavengers (e.g., triphenyl phosphine), inhibitors (e.g., hydroquinone, methyl ether hydroquinone, aluminum tris (N-nitroso-N-phenylhydroxylamine) and butylated hydroxy toluene), optical brighteners (e.g., Uvitex OB from Ciba-Geigy), dispersion aids (e.g., polyethyleneimine), waxes (e.g., Everglide UV 691 polyethylene wax emulsion in monomer from Shamrock), mineral and polymeric fillers, nanofillers dispersed in (meth) acrylate resins or monomers, silica organosols (e.g., Highlink® OG 100 from Clariant), fibers (e.g., polyamide or polynitrile fibers), rosins (e.g., glycerol esters of hydrogenated rosins), solvents (e.g., ethyl acetate, acetone and isopropyl alcohol), adhesion promoting monomers (e.g., methacroyloxy ethyl phthalate), and colorants (e.g., barium, calcium or aluminum lakes, iron oxides, talcs, carmine, titanium dioxide, chromium hydroxides, ferric ferrocyanide, ultramarines, titanium dioxide coated mica platelets, and bismuth oxychlorides). The BISGMA urethane based nail coating of the present invention, even when heavily pigmented, reacts with UV radiation. A coat of the material cures with a standard ultraviolet nail light in less than approximately two minutes. Moreover, it cures with visible light, such as from a dental curing unit, in less than approximately 20 seconds.

Finishing Materials of the Present Invention

The present invention additionally comprises nail finishing materials that complement the actinic radiation curable coatings. While the coating is cured with actinic radiation, oxygen inhibition causes the surface of the coating typically to be tacky. Isopropyl alcohol is generally used to remove the tacky layer. While this is generally a somewhat effective method, the alcohol may increase skin sensitization in a user. The finishing material compositions of the present invention may be applied with a cotton swab or pad, or sprayed directly onto the nail to remove the sticky surface without increasing skin sensitization and beneficially by introducing a high gloss surface not achievable with the alcohol. The nail is then rubbed or buffed, for example, with a clean cloth, resulting in a clean smooth surface. The nail treatment may be considered complete at this point. If a higher gloss is desired, a topcoat of a solvent-based cellulose material may be applied to complete the procedure.

The finishing materials of the present invention are disclosed in Table 2. The finishing materials of the present invention preferably comprise: 1) between approximately 30 and approximately 90 percent by weight and preferably between approximately 50 and approximately 80 percent by weight, of a biocompatible solvent such as but not limited to acetone, ethyl alcohol, ethyl acetate, isopropyl alcohol, and methyl ether ketone; 2) between approximately 5 and approximately 40 percent by weight and preferably between approximately 10 and approximately 30 percent by weight, of a vegetable oil such as but not limited to castor oil; and 3) between approximately 5 and approximately 30 percent by weight and preferably between approximately 10 and approximately 20 percent by weight, of a lanolin based material such as but not limited to PEG-75 lanolin, Laneto 50 lanolin from RITA Corp., hydroxylated lanolin, hydrogenated lanolin and other lanolin derivatives, or other emollients known in the art. A fragrance such as but not limited to lavender oil or orange oil, may also be added to makes this material more appealing to the consumer. Some representative formulas for the finishing materials are shown in Table 2.

TABLE 2

| Examples 3 through 6 (quantities in grams) | | | | |
|---|---|---|---|---|
| Example | 3 | 4 | 5 | 6 |
| Ethyl Alcohol | — | 10.56 | — | — |
| Isopropyl alcohol | 3.82 | — | 14.02 | 49.83 |
| Laneto 50 | — | 2.25 | 2.89 | 8.97 |
| Lanolin | | | | |
| Castor Oil | 3.82 | 11.50 | 3.05 | 8.66 |
| Orange Oil | — | — | 0.0125 | — |
| Lavender Oil | — | — | — | 0.62 |

Method of Creating a Semi-Permanent Nail Enhancement

In the preferred embodiment, coating composition of the present invention is applied to a natural nail, (the nail may be filed on the top surface to remove oils and create a surface for bonding). A bond-enhancing adhesive material may be applied to part or the entire surface of the nail, preferably beginning at the cuticle. (The solvent in the pre-bond finishing material is allowed to evaporate over a given period, leaving a tacky surface.) An optional actinic radiation curable white tipping coating is then applied to the ends of the nail and cured if the French manicure look is desired. A clear or light pink coating material is applied to the nail, preferably starting at the cuticle and moving toward the white tipping, and cured. The coated nail is then filed to a smooth surface. A clear coating material is then preferably applied over the entire nail surface and cured. An optional second coat or multiple clear coats may be applied. The finishing material of the present invention is then applied to remove the top sticky layer, and the coated nail is preferably buffed to a high gloss shine. Other colors of coatings are anticipated and may be used in any number of combinations or alone.

In an alternative embodiment, materials of the present invention are applied to a nail-tip that is attached to a natural nail, (the nail may be filed on the top surface to remove oils and create a surface for bonding). The nail-tip is applied to the natural nail with, for example, but not limited to, a glue (e.g. cyanoacrylate glue) known in the art. After the glue has set, the nail-tip may be filed. A bond-enhancing material of the present invention is optionally applied to the natural nail, preferably beginning at the cuticle to the front edge of the nail-tip. It is not generally necessary to apply the bond-enhancing material to the surface of the nail tip, however it may be applied, if desired. As an example, an optional actinic radiation curable white tipping coating is applied to the ends of the nail-tip and cured. A clear or light pink coating material is applied to the entire nail, preferably starting at the cuticle and moving toward the white tipping, and cured. The coated nail is then preferably filed to a smooth surface. A clear coating material is preferably applied over the entire nail surface and cured. Application of a second or other multiple clear coats is optional. The finishing material is preferably applied to remove the top sticky layer, and the coated nail is then preferably buffed to a high gloss shine.

Inventive methods of applying colored coating materials of the present invention are similar to the methods described above for the clear-white tipped nails except, for example, that a second final clear coat optionally replaces a colored coating. Application of an optional second colored coat is applied for best results.

TABLE 3

| | Examples 7 through 15 (quantities in grams) | | | | | | | | |
|---|---|---|---|---|---|---|---|---|---|
| Ingredient | 7 Prior Art | 8 Prior Art | 9 | 10 | 11 | 12 | 13 | 14 | 15 |
| UDMA resin | 3.01 | 3.79 | 12.56 | — | — | — | — | — | — |
| Ethoxylated BPADMA | 4.04 | 4.61 | 6.00 | — | — | — | — | — | — |
| Benzildimetyl ketal | .0316 | — | .04 | .0771 | .0211 | .1920 | .0470 | .0392 | .00283 |
| Butoxyethyldimethyl aminobenzoate | .09 | — | — | — | — | — | — | — | — |
| Dimethylaminoethyl (meth)acrylate | — | .13 | — | — | — | .51 | .13 | .1074 | .0776 |
| Octyl-para-dimethyl aminobenzoate | — | — | .14 | .2264 | .0649 | — | — | — | — |
| Ethyldimethyl amino benzoate | — | — | — | — | — | — | — | .0311 | — |
| Ethyl 2,4,6-trimethyl benzoylphenyl phosphinate | — | .09 | .17 | .2459 | .0674 | .52 | .13 | .11 | .08 |
| Neoalkoxy titanate | — | — | .02 | .0300 | .0084 | .11 | .0300 | .0248 | .0179 |
| D & C Red #33 | — | — | — | — | .0136 | — | — | — | — |
| D & C Red #6 Barium Lake | — | — | — | — | — | — | — | .0495 | — |
| D & C Red #7 Calcium Lake | — | — | — | — | — | — | — | .1127 | — |
| Ext. D & C Violet #2 | — | — | — | — | — | — | — | .0015 | — |

TABLE 3-continued

Examples 7 through 15 (quantities in grams)

| Ingredient | 7 Prior Art | 8 Prior Art | 9 | 10 | 11 | 12 | 13 | 14 | 15 |
|---|---|---|---|---|---|---|---|---|---|
| Titanium dioxide coated mica platelets | — | — | — | — | — | — | — | — | .0750 |
| Titanium dioxide | — | — | .07 | — | — | — | .0374 | .0300 | .0075 |
| N-ethyl-o & p toluenesulfonamide | — | — | 1.00 | 2.10 | 0.59 | 7.09 | 1.75 | 1.46 | 1.05 |
| Mono(Methacryl-oyloxyethyl) Phthalate | — | — | — | — | — | 2.67 | .66 | .55 | .40 |
| (meth)acrylated-aliphatic Urethane Resin | — | — | — | 4.50 | 2.52 | 30.43 | 7.46 | 6.22 | 4.50 |
| BISGMA Urethane Resin of the Invention | — | — | — | 22.83 | 5.15 | 59.8 | 14.54 | 12.13 | 8.77 |

The formulas shown in Examples 7 and 8 illustrate typical UV radiation curable resin systems, known in the art. The materials of Examples 7 and 8 typically cure under UV radiation in about two to about three minutes. The formulas of Examples 9 to 15 illustrate the coating materials of the present invention. The material of Example 9 is highly reactive to UV radiation and will cure in less than two minutes, even with a high level of titanium dioxide white pigment. The formulas of Examples 10 through 12 are for coating materials with the BISGMA urethane resin and the polyether based (meth)acrylated aliphatic urethane resin. The latter resin having a viscosity greater than approximately 80,000 cps. These materials are easily applied and exhibit a creamy consistency, which do not run on the nail during application, unlike the prior art materials of Examples 7 and 8. The materials of Examples 10 through 12 exhibit clear and translucent pink shades that are easily cured with UV radiation in less than two minutes to a durable nail coating. The formula of Example 13 is for a UV radiation cured opaque white material useful for covering the very end of the natural nail or nail tip to give the French manicure look. The formula of Example 14 is for a very highly colored material and the formula of Example 15 is for a shimmering or opalescent material, both of which cure to form durable coatings when exposed to UV radiation for approximately two minutes.

DESCRIPTION OF EXAMPLES 16 THROUGH 21

Table 4 lists formulas for Examples 16 through 21. The formulas of Examples 16, 17, and 18 comprise a substantially clear material for application to a nail. The formulas of Examples 16, 17, and 18 harden in approximately 1 to approximately 2 minutes under ultraviolet radiation. The formulas of Examples 19, 20, and 21 comprise a substantially opaque white material for application to a nail. The formulas of Examples 19, 20, and 21 harden in approximately 2 to approximately 3 minutes under ultraviolet radiation. The formulas of Examples 16–21 are further optionally useful for creating a free edge of a nail. In general, the formulas of Examples 18 and 19 are less brittle than the formulas presented in the '986 application. Overall, the materials of Examples 16 through 21 are optionally useful in creating a high gloss natural look and giving strength to the nails.

TABLE 4

Examples 16 through 21 (quantities in grams)

| Ingredient | 16 | 17 | 18 | 19 | 20 | 20A | 20B | 21 |
|---|---|---|---|---|---|---|---|---|
| BISGMA Urethane resin | 22.83 | 59.8 | 2.56 | 7.08 | 14.54 | 88.65 | 88.85 | 6.25 |
| (meth)acrylated polyether-urethane Resin | 4.5 | 30.43 | 3.57 | 9.80 | 7.46 | 44.0 | 44.13 | 3.58 |
| Ethyl toluenesulfonamide | 2.10 | 7.09 | 0.41 | 1.12 | 1.75 | 10.7 | 10.7 | 0.84 |
| Octyl-para-dimethylamino Benzoate | 0.2264 | — | — | — | — | — | — | — |
| Benzildimethylketal | 0.0771 | 0.1920 | 0.0131 | 0.0358 | 0.0470 | 0.28 | 0.28 | 0.0227 |

TABLE 4-continued

Examples 16 through 21 (quantities in grams)

| Ingredient | 16 | 17 | 18 | 19 | 20 | 20A | 20B | 21 |
|---|---|---|---|---|---|---|---|---|
| Ethyl 2,4,6-trimethyl-benzoyl-Phenylphosphinate | 0.2459 | 0.52 | 0.0346 | 0.1160 | 0.13 | 0.74 | 0.74 | 0.062 |
| Neoalkoxy-titanate | 0.0300 | 0.11 | 0.0092 | 0.0209 | 0.0300 | 0.19 | 0.19 | 0.12 |
| Fumed silica | — | — | — | — | — | — | — | 0.42 |
| Hydrogenated Rosin | — | — | 0.0281 | 0.0768 | — | — | — | — |
| Ethyl Acetate | — | — | 0.0138 | 0.0378 | — | — | — | — |
| Mono(methacryloyl-Oxyethyl) phthalate | — | 2.67 | 0.1932 | 0.5143 | 0.66 | 4.03 | 4.03 | 0.33 |
| Dimethyl-aminoethyl (meth)acrylate | — | 0.51 | 0.0345 | 0.0967 | 0.13 | 0.74 | 0.74 | 0.0621 |
| Iron Oxide and mica | — | — | — | — | — | 0.30 | 0.12 | — |
| D & C Red #7 Calcium Lake | — | — | — | — | — | 0.15 | — | — |
| Titanium dioxide | — | — | — | 0.00947 | 0.0374 | 0.30 | 0.30 | 0.0604 |

Examples 22 through 26 list formulas that can be applied to natural or artificial nails prior to the application of radiation cured nail coatings to aid bonding.

TABLE 5

Examples 22 through 26 (quantities in grams)

| Ingredient | 22 | 23 | 24 | 25 | 26 |
|---|---|---|---|---|---|
| Acetone | 8.52 | 52.43 | 8.18 | 11.81 | 2.38 |
| Sarbox 500E50 | 1.52 | 11.18 | 1.75 | 2.53 | 0.51 |
| Hydrogenated Rosin | — | 11.33 | 1.78 | 2.53 | 0.51 |
| BISGMA Urethane Resin | — | — | 0.46 | 0.33 | — |
| (meth)acrylated polyether urethane resins | — | — | 0.35 | 1.67 | — |
| Ethyl 2,4,6-trimethylbenzoyl-Phenylphosphinate | — | — | 2.38 | 0.0111 | — |
| Dimethylaminoethyl (meth)acrylate | — | — | 0.0153 | 0.0112 | — |
| Ethyl toluenesulfonamide | — | — | 0.15 | 0.1561 | — |
| Neolkoxy titanate | — | — | 0.0032 | 0.0022 | — |
| Mono(methacryloyl-oxyethyl) phthalate | — | — | 0.0919 | 0.0691 | — |
| Ethyl Acetate | — | — | 0.0131 | — | — |
| Tosylamide Epoxy Resin | — | — | — | 4.66 | 0.98 |

Method of Creating a Semi-Permanent Nail Enhancement with Color

The following method describes the use of Examples 16–18, 20A and 20B to create a semi-permanent nail enhancement with color that can be filed off, but not soaked off:

Step 1: File natural nail to remove oil and shine to minimize any subsequent lifting.
Step 2: If desired, select a nail tip and/or nail form:
  Step 2a: Apply the nail tip or form using, for example, an adhesive (glue)
  Step 2b: If using a nail tip, cut the nail tip to a desired shape
  Step 2c: Blend (e.g., file) the nail tip to natural nail
Step 3: Select a bond agent, for example, from one of the formulas presented in Examples 1–2A or Examples 22–26.
Step 4: Apply the bond agent to natural nail, which comprises a nail tip and/or nail form. Do not cure.
Step 5: Select clear material, for example, from one of the formulas presented in Examples 16 through 18.
Step 6: Apply the selected clear material in one to two coats curing clear material between coats for at least approximately 1 to approximately 2 minutes.
Step 7: Remove residue from nail with, for example, alcohol.
Step 8: If a nail form was applied then:
  Step 8a: Remove the nail form.
Step 9: Shape and buff cured material applied to the nail into a desired shape.
Step 10: Select a formula from formulas presented in Examples 16, 17, 20A or 20B.
Step 11: Apply the selected formula from Step 10 on the already treated nails; preferably apply to one to two fingers at a time; preferably, use a brush and only one side of brush to allow for a closer approach to cuticle.
Step 12: Cured the applied formula from Step 11.
Step 13: Optionally repeat Steps 11 and 12.
Step 14: Remove any residue from the coated nails with, for example, alcohol or finishing compounds of Examples 3–6.

Step 15: Apply a solvent evaporation based high sheen coatings for nails for greater shine if desired.

Method of Creating a Semi-Permanent Nail Enhancement with a French White Look

The following method describes the use of Examples 16, 17, 18, 19, 20, and 21 to create a semi-permanent nail enhancement with a French White Look that can be filed off, but not soaked off:

Step 1: File natural nail to remove oil and shine to minimize any subsequent lifting.

Step 2: If desired, select a nail tip and/or form:
Step 2a: Apply the nail tip or nail form;
Step 2b: If using a nail tip, then cut the nail tip to a desired shape; and
Step 2c: Blend the nail tip to natural nail.

Step 3: Select a white tipping agent from, for example, the formulas presented in Example 19, 20, or 21.

Step 4: Apply white tipping to the nail form or nail tip, creating a smile line at the free edge.

Step 5: Cure the applied white tipping agent for approximately 2 minutes.

Step 6: Optionally repeat Step 4 and 5 to form a more definite smile line at free edge.

Step 7: Select a bond agent, for example, from one the formulas presented in Examples 1–2A, or 22 through 26.

Step 8: Apply the selected bond agent to natural nail comprising the applied nail form and/or nail tip. Do not cure.

Step 9: Select clear material, for example, from one of the formulas presented in Examples 16 through 18.

Step 10: Apply the selected clear material in approximately one to approximately two coats, curing between coats for at least approximately one to approximately 2 minutes.

Step 11: Remove any residue from the treated nail with, for example, alcohol.

Step 12: If nail form was applied then:
Step 12a: Remove the nail form.

Step 13: Cure the applied material;

Step 14: Shape and buff cured material applied to the nail into a desired shape.

Step 15: Select a final coating material from one of the formulas in Examples 16, 17, 18, 20A or 20B.

Step 16: Apply the selected final coating material from Step 15 onto the treated nails (per Steps 1 through 13) applying the coated material, for example, to one to three fingers at a time.

Step 17: Cure the applied coating material for approximately 1 to approximately 2 minutes.

Step 18: Repeat Step 16 and 17 until all nails have been coated.

Step 19: Remove residue from the coated nail with, for example, alcohol or finishing compounds from Examples 3–6.

Step 20: Apply a solvent evaporation based high sheen coatings for nails if greater shine is desired.

Method of Creating a Semi-Permanent Nail Enhancement with a French White Look Using an Electric File The following method describes the use of Examples 16, 17, 18, 19, 20, and 21 to create a semi-permanent nail enhancement with the French White Look using the electric file that can be removed by filing, but not soaked off:

Step 1: File natural nail to remove oil and shine to minimize any subsequent lifting.

Step 2: If desired, select a nail tip and/or nail form:
Step 2a. Apply the nail tip or form
Step 2b. If using a nail tip, cut the nail tip to desired length; and
Step 2c. Blend and shape nail tip to natural nail Step 3: Select a bond agent, for example, from one of the formulas presented in Examples 1–2A or 22–26.

Step 4: Apply the bond agent to natural nail, which comprises a nail tip and /or nail form. Do not cure.

Step 5: Select clear material, for example, from one of the formulas presented in Example 16–18.

Step 6: Apply the selected clear material in one or two coats, curing the clear material between coats for at least approximately 1 to approximately 2 minutes.

Step 7: Remove any residue from the nail with, for example, alcohol.

Step 8: If a nail form was applied then:
Step 8a. Remove nail form

Step 9: Shape and buff cured material applied to nail into a desired shape.

Step 10: Creating a French look use an electric file, removing clear material previously applied in Step 6 at free edge only, to create a line and/or ditch.

Step 11: Select a formula from Example 19, 20 or 21 to fill in area previous filed out with an electric file.

Step 12: With selected formula, apply material at area where product was removed to create a white French tip.

Step 13: Cure formula applied in Step 12, for approximately for 2 to approximately 3 minutes.

Step 14: Remove any residue from the coated nails with, for example, alcohol.

Step 15: File and buff nail lightly to smooth out any unevenness of nail.

Step 16: Select a final coating material from one of the formulas in Examples 16, 17, 18, 20A, or 20B.

Step 17: Apply the material selected from Step 16, for final coat. Applying only to one to two fingers at a time.

Step 18: Cure material applied in Step 17 for approximately one to approximately two minutes. Repeating Step 17 until all nails are finished.

Step 19: Remove residue from the coated nails with, for examples, alcohol or finishing compounds from Examples 3–6.

Step 20: Apply a solvent evaporation based high sheen coatings for nails if greater shine is desired.

Examples 7 through 32, described herein, give formulas for materials suitable for clear, French White Look, or colored radiation curable coatings. These examples optionally comprise clear or colored protective coatings on natural nails or artificial nails.

TABLE 6

Examples 27 through 32 (quantities in grams)

| Ingredient | 27 | 27A | 28 | 28A | 29 | 30 | 31 | 32 |
|---|---|---|---|---|---|---|---|---|
| BISGMA | — | 0.17 | 3.0 | 3.0 | 1.94 | 2.95 | 109.7 | 1.82 |
| Urethane resin (meth)acrylated polyether urethane Resins | 5.72 | 0.92* | 15.74 | 5.28 | 9.41 | 15.50 | 602.8 | 9.56 |
| Ethyl toluenesulfonamide | 1.14 | 0.06 | 1.0 | 0.6 | 0.83 | 0.99 | 56.3 | 0.61 |
| Hydroxyethyl (meth)acrylate | 0.59 | — | — | — | 0.39 | — | — | — |
| Benziidimethylketal | 0.0129 | 0.002 | 0.0400 | — | — | 0.0390 | 1.52 | 0.024 |
| Ethyl 2,4,6-trimethylbenzoyl-Phenylphosphinate | 0.0325 | 0.006 | 0.10 | — | — | 0.0986 | 4.0 | 0.061 |
| Trimethylolpropane tri(meth)acrylate | — | — | — | — | 0.10 | — | — | — |
| Blend of 2,4,6-Trimethylbenzoyl-Diphenylphosphine-Oxide and methylbenzo-Phenone derivatives | — | — | — | — | 0.0634 | — | — | — |
| 1-[4-(4-benzoylphenyl-sulfanyl) phenyl]-2-methyl-2-(4-methylphenylsul-fanyl) propan-1-one | — | — | — | 0.05 | — | — | — | — |
| Neoalkoxy titanate | 0.0065 | 0.002 | 0.0200 | 0.01 | 0.0320 | 0.0205 | 0.8 | 0.019 |
| Mono(methacryloyl-Oxyethyl) phthalate | — | 0.035 | — | — | 0.54 | 0.59 | 24.8 | 0.37 |
| Dimethylaminoethyl (meth)acrylate | 0.0330 | 0.006 | 0.10 | 0.05 | 0.0609 | 0.0986 | 4.0 | 0.061 |
| Hydrogenated Rosin | — | 0.093 | — | — | — | 0.33 | — | 0.52 |
| Ethyl Acetate | — | 0.206 | — | — | — | 0.16 | — | 1.20 |
| D & C Red #7 Calcium Lake | — | — | — | — | 0.0011 | 0.1271 | — | — |
| D & C Red #6 Barium Lake | — | 0.012 | — | — | — | 0.0218 | — | — |
| Yellow #10 | — | 0.001 | — | — | — | — | — | — |
| D & C Red #17 | — | 0.001 | — | — | — | — | — | — |
| D & C Violet #2 | — | 0.001 | — | — | — | 0.0107 | — | — |
| Titanium dioxide coated mica platelets | — | 0.001 | — | — | 0.0740 | — | — | — |
| Iron oxide and mica | — | — | — | — | 0.0125 | — | — | — |
| Titanium dioxide | — | — | — | — | 0.0409 | 0.0426 | — | 0.1014 |

*Blend of three molecular weight components

EXAMPLE 32A

Mixing Standard Nail Polish with Soak-Off Gel to Create a Removable Color Gel Nail Coating A ratio of 1 part nail polish to 2 parts soak-off UV gel from examples 27, 28, 28A, 31, or 32 was mixed. It was also found that 1½ parts nail polish to 2½ parts soak-off UV gel from example 27, 28, 28A, 31, or 32 is useful. These mixtures created UV gel polish, which was easily applied with a brush to artificial and natural fingernails and toenails. This gel polish allowed for a customized color, dried instantly with UV irradiation of two minutes, strengthened and smoothed out the unevenness of natural nails and gave a higher shine. Furthermore, the cured gel polish lasted longer than standard nail polish and was easier to remove using the foil soak-off method.

Method of Creating a Temporary Natural Nail Enhancement with Color

The following method describes the use of formulas of Examples 22 through 32A to create a temporary natural nail enhancement with color that can be soaked off:

Step 1: File natural nail with a 220 grit file, to remove oil and shine and to minimize any subsequent lifting.

Step 2: Apply nail dehydrator (drying agent) to swab or nail wipe.

Step 3: Wipe nails with dehydrator to remove dust and minimize lifting.

Step 4: Apply a formaldehyde or non-formaldehyde traditional solvent evaporation base coat or a bond agent, for example, from one of the formulas presented in Examples 1–2A or 22–26 to natural nail and allow to dry for two minutes.

Step 5: Apply nail forms to the fingers under the free edge of the nail if desired to lengthen natural nails.

Step 6: Select a formula of Examples 27, 28, 28A, or 31.

Step 7: A small amount of the selected formula is applied to one side of a nail brush and then brush close to the cuticle to create a straight even line. The rest of the formula is brought down to the free edge and past it to cover and extend the nail.

Step 8: Cure the coating using UV radiation for approximately 2 minutes.

Step 9: Remove the nail forms.

Step 10: Remove any tackiness from the coated nails with, for example, alcohol.

Step 11: File and/or buff the nail into a desired shape.

Step 12: Remove dust.

Step 13: Select a color formula of Examples 27A, 29, 30, 32 or 32A.

Step 18: Polish the selected formula onto the entire surface.

Step 19: Cured the polished formula for approximately two minutes using UV radiation.

Step 20: Remove any tackiness from the polished nail surface using, for example, alcohol or finishing compounds from Examples 3–6.

Step 21: Apply a solvent evaporation based high sheen coatings for nails if greater shine is desired.

Method of Creating a Temporary Natural Nail Enhancement with the French White Look The following method describes the use of formulas of Examples 22 through 32 to create a temporary natural nail enhancement with the French White Look that can be soaked off:

Step 1: File natural nail with a 220 grit file, to remove oil and shine and to minimize any subsequent lifting.

Step 2: Apply nail dehydrator (drying agent) to swab or nail wipe.

Step 3: Wipe nails with dehydrator to remove dust and minimize lifting.

Step 4: Apply a formaldehyde or non-formaldehyde traditional solvent evaporation base coat or a bond agent, for example, from one of the formulas presented in Examples 1–2A or 22-26 to natural nail and allow to dry for two minutes.

Step 5: Apply nail forms to fingers under free edge of the natural nail.

Step 6: Select a formula from Example 32.

Step 7: Apply selected formula from Step 6 to free edge of natural nail. Preferably apply to one to two fingers at a time.

Step 8: Cure the applied material for approximately 2 minutes.

Step 9: Select a material from Examples 27, 28, 28A, 29, or 31.

Step 10: Apply selected material like polish on one to two fingers at a time.

Step 11: Cure material 2 minutes.

Step 12: Optionally repeat Steps 10 and 11 for additional coatings.

Step 13: Remove nail forms.

Step 14: Remove any tackiness from the coated nails with, for example, alcohol.

Step 15: Shape and buff cured material lightly with a 220 grit file, into a desired shape.

Step 16: Select a final coating material from Examples 27, 28, 28A, 29, or 31.

Step 17: Apply final coating material from step 16 on one to two nails at a time.

Step 18: Cure the applied material for approximately 2 minutes.

Step 19: Wipe residue from the coated nails with, for example, alcohol or finishing compounds from Examples 3–6.

Step 20: Apply a solvent evaporation based high sheen coatings for nails if greater shine is desired.

METHODS OF USING EXAMPLES 22 THROUGH 32A

The following method is applicable to any type of nail, the method as described in this embodiment, refers to toenails (in particular, the formula of Example 27A is preferred for toenail applications):

Step 1: Apply a nail dehydrator, for example, a drying agent to a cloth, wipe, etc.

Step 2: Wipe each toenail with the dehydrator to remove oil, lotion, etc.

Step 3: File each toenail to remove oil and shine and to minimize lifting.

Step 4: Apply a formaldehyde or non-formaldehyde traditional solvent evaporation base coat or a bond agent, for example, from one of the formulas presented in Examples 1–2A or 22–26 to natural nail and allow to dry for two minutes.

Step 5: Select a formula from, for example, one of the formulas presented in Examples 27 through 32A.

Step 6: Apply the selected color formula, in a manner similar to application of a polish, to approximately one to approximately two toenails at a time; preferably apply the selected color formula on one side of a flat nail brush to allow for a closer approach to the cuticle; secure seal at free edge of natural nail to prevent lifting of product.

Step 7: Cure the applied formula for approximately 2 minutes.

Step 8: Repeat Steps 6 and 7 until all toenails are coated.

Step 9: Remove any residue from the coated toenails with, for example, alcohol or finishing compounds from Examples 3–6.

Step 10: Apply a solvent evaporation based high sheen coatings for nails if greater shine is desired.

Method for Creating Semi-Permanent Nail Enhancements with Removable Color Coatings This method describes the use of formulas of Examples 27 through 32A for removable color coatings on semi-permanent artificial nails. For example, these formulas are useful in conjunction with nails prepared according to "Method of Creating a Semi-Permanent Nail Enhancement."

Step 1: A finished nail from the "Method of Creating a Semi-Permanent Nail Enhancement" is lightly buffed.

Step 2: Apply a formaldehyde or non-formaldehyde traditional solvent evaporation base coat.

Step 3: Allow the base coat to dry for two minutes.

Step 4: Select a color formula from, for example, one of the formulas presented in Examples 27A, 29, 30 or 32A.

Step 5: The selected color gel is applied to a nail with a flat brush, starting close to the cuticle, creating a straight line around cuticle, and pulling down on rest of nail until all nail and free edge is covered with color.

Step 6: The applied gel coating is cured for approximately two minutes with UV radiation.

Step 7: An optional second coating of color is applied in the same fashion and cured for two minutes.

Step 8: Remove any residue from the coated nails with, for example, alcohol or finishing compounds from Examples 3–6.

Step 9: Apply a solvent evaporation based high sheen coating for nails if greater shine is desired.

The formulas presented in Examples 33 through 35 are useful in soaking off the coatings prepared by this aforementioned methods—"Method of Creating a Temporary Natural Nail Enhancement with Color", "Method of Creating a Temporary Natural Nail Enhancement with the French White Look", "Method of Using Examples 22 through 32", and "Method for Creating Semi-Permanent Nail Enhancements with Removable Color Coatings".

TABLE 7

Examples 33 through 35 (quantities in grams).

| Ingredient | 33 | 34 | 35 |
| --- | --- | --- | --- |
| Acetone | 7.09 | 6.38 | 6.86 |
| Squalene | 0.16 | 0.29 | 0.15 |
| Dipropylene Glycol Methyl ether | — | 1.07 | — |
| Lanolin | — | — | 0.72 |

METHODS OF USING EXAMPLES 33 THROUGH 35

The following embodiment describes a method for removing material comprising, for example, formulas from Examples 27 through 32A, from toenails and/or fingernails:

Step 1; Select a soak-off agent from, for example, one of the formulas of Examples 33 through 35.

Step 2: Apply the selected soak-off agent to a carrier, for example, a cloth, wipe, etc.; preferably a wipe comprising approximately one square inch.

Step 3: Place the carrier comprising the selected soak-off agent onto a nail.

Step 4: Secure the carrier to the nail with, for example, a wrap, for example, but not limited to, a piece of aluminum comprising approximately 16 square inches (e.g., approximately 4 inches square).

Step 5: Let the secured carrier set for approximately 10 minutes.

Step 6: Remove the secured carrier.

Step 7: Remove the soak-off agent treated material from the nail.

Applying Soak-off Removable Color Gel Coatings on Powder/Liquid Acrylic Systems

Step 1: Follow the steps in applying acrylic to natural nail or a re-balance.

Step 2: Once powder/liquid acrylic is applied, apply a nail dehydrator (drying agent) to a swab or wipe.

Step 3: Wipe nails with dehydrator to remove dust and to minimize lifting.

Step 4: On top of the powder/liquid acrylic, apply coat of clear gel from examples 16, 17, 18, 20A, or 20B with nail brush, making sure to cover entire nail and sealing at free edge.

Step 5: Cure 2 minutes in UV light, remove from light and wipe with alcohol using a lint free swab or nail wipe to remove tacky residue.

Step 6: Use a white buffing block, lightly buff previously cured material to create a dull surface.

Step 7: Apply a regular base coat to nails and let dry.

Step 8: Select a Soak-off Color to be applied from examples 27A, 29, 30, 32, or 32A. Apply like polish on one to two nails at a time. Cure for 30 seconds. Preferably, apply product on one side of a flat nailbrush as this allows for a closer approach to cuticle. Secure seal at free edge of natural nail to prevent lifting. Remove any gel that has hit the skin or cuticle with a toothpick before curing.

Step 9: Once all nails have first coat applied, cure an extra 1 to 2 minutes more.

Step 10: A second coat is then applied closer to cuticle to overlap first coat, and cured for 1 to 2 minutes.

Step 11: Remove any tackiness from nail with isopropyl alcohol.

Step 12: Apply one coat of standard clear nail polish and let dry 2 minutes.

Method of Lengthening or Improving the Appearance of Selected Nails

This method describes the use of formulas of Examples 27 through 32A with artificial nail tips to lengthen or improve the appearance of nails that may be shorter, hard to grow, broken, or damaged to create a balanced appearance of all ten nails:

Step 1: Buff the natural nail with a white block to remove the shine.

Step 2: Apply a nail tip and cut and blend into the natural nail.

Step 3: Apply a formaldehyde or non-formaldehyde traditional solvent evaporation base coat or a bond agent, for example, from one of the formulas presented in Examples 1–2A or 22–26 to natural nail and allow to dry for two minutes.

Step 5: Select a material from the formulas of Examples 27, 28, or 31.

Step 6: Apply the selected formula to the tip and natural nail.

Step 7: Cure the applied formula for approximately 1 to approximately 2 minutes using UV radiation.

Step 8: Optionally apply a second coat for more strength and/or a higher arch in the nail.

Step 9: Remove any tackiness with alcohol.

Step 10: File and/or buff the nail to a more desirable shape.

Step 11: Optionally top the nail with a clearcoat and/or colored coating selected from the formulas of Examples 27 through 32 and cure for two minutes.

Step 12: Remove any residue from the coated nails with, for example, alcohol or finishing compounds from Examples 3–6.

Step 13: Apply a solvent evaporation based high sheen coating for nails if greater shine is desired.

Temporary Nail Tip and/or Sculpted Nail with Natural Nail Enhancements

Step 1: File natural nail with a 220-grit file, to remove oil and shine and to minimize any subsequent lifting.

Step 2: Apply a nail dehydrator (drying agent) to a swab or wipe.

Step 3: Wipe nails with dehydrator to remove dust and to minimize lifting.
Step 4: Select a nail tip and/or nail form for sculpting:
   Step 4a: Apply the nail tip or form
   Step 4b: If using a nail tip; cut the nail tip to a desired shape.
   Step 4c: Blend the nail tip to the natural nail.
Step 5: If using a nail form for sculpting, apply nail form to finger under free edge of the nail.
Step 6: Select a base coat, for example, from one of the formulas presented in the base coat agent examples mentioned above.
Step 7: Apply the base coat to the natural nail, which comprises a nail tip and/or nail form. Let dry 1 to 2 minutes.
Step 8: Select clear material, for example, from one of the formulas presented in the clear soak-off material examples given above.
Step 9: Apply the selected clear material like polish in one to two coats curing clear material between coasts for at least approximately 1 to approximately 2 minutes.
Step 10: Remove the nail forms.
Step 11: Remove any tackiness from the UV coated nails with, for example, alcohol.
Step 12: Lightly shape and buff cured material applied to the nail into a desired shape.
Step 13: Select a formula from Examples. These examples should include both color and clear material for soak off.
Step 14: Apply Example selected from Step 13, like polish on one to two nails at a time. Preferably, apply product on one side of a flat nailbrush. This allows for a closer approach to the cuticle. Secure seal at free edge of natural nail to prevent lifting. Remove any gel that on the skin or cuticle with a toothpick before curing.
Step 15: Cure the applied formula from Step 14 for 2 minutes.
Step 16: An optional second coating, from Example 14, is applied in the same fashion and cured 2 minutes.
Step 17: Remove any tackiness from nail with, for example, alcohol.
Step 18: Apply a solvent evaporation based high sheen coating for nails.

Removal of Nail Tip or Sculpted Nail with Natural Nail Enhancements

Step 1: Select a soak off agent from, for example, one of the formulas of the soak-off agent examples, see above.
Step 2: Apply the selected soak off agent to a carrier, for example, a cloth, a wipe, etc. Preferably use a wipe comprising approximately one square inch.
Step 3: Place the carrier comprising the selected soak off agent onto a nail tip or sculpted nail.
Step 4: Secure the carrier to a nail tip or sculpted nail with a wrap, for example, but not limited to, a piece of aluminum comprising approximately 16 square inches (e.g. approximately 4 inches square).
Step 5: Let the secured carrier set for approximately 10 minutes.
Step 6: Remove the secured carrier.
Step 7: Remove any material that has loosened from the nail with, for example, a wipe, orange wood stick, or a nail file.
Step 8: Additional soaking can be applied to a nail to remove areas that have not loosened. Repeat steps 2 through 4, and let soak for only 5 minutes and remove the secured carrier.
Step 9: Remove the soak off agent treated material from the nail with, for example, a nail cleanser. Soak fingers in water for 3 to 5 minutes.

Home Care Maintenance for Natural Nail Enhancements

Step 1: Buff nail with a buffing block to remove oils and shine and to minimize lifting.
Step 2: Apply a nail dehydrator (drying agent) to a swab or wipe.
Step 3: Wipe nails with dehydrator to remove dust and to minimize lifting.
Step 4: Select a color from one of the colored formula examples (this is preferably a soak clear or colored gel). The color formula selected should be the same or changed to a color staying close to color already existing on nails.
Step 5: From material selected in Step 4, start at cuticle area, fill gap that has grown out and brush down to cover entire nail. Preferably apply to one to two fingers at a time; preferably using a flat nailbrush and applying product to only one side of brush to allow for a closer approach to the cuticle.
Step 6: Cure the applied formula from Step 5 for 2 minutes.
Step 7: An optional second coating, from Step 4, is applied in the same fashion and cured 2 minutes.
Step 8: Remove any tackiness from nail with, for example, alcohol.
Step 9: Apply a solvent evaporation based high sheen coating for nails.

The Home Maintenance on Natural Nail Enhancements can be repeated up to three times before going to a salon professional.

EXAMPLE 36

Coated filler was prepared for incorporation into the radiation curable nail coatings of the present invention. A resin blend of 66 grams of Nupol 46–4005 and 30 grams of triethylene glycol dimethacrylate was mixed. Then 0.5 grams of ethyl 2,4,6-trimethylbenzoylphenylphosphinate was added and mixed in. Next 9 grams of amorphous silicon dioxide was added to 44 grams of the resin blend until a thick paste resulted. This mixture was heated overnight at 50° C. overnight. The next day the mixture was rolled thin between two pieces of plastic and cured in the sunlight for several hours. After thorough curing, the plastic was removed from the cured material, which was broken into pieces and then ground into a fine powder. Then 1.2 grams of the fine powder was mixed into 2.6 grams of radiation curable nail coating of example 13 to give a thick nail composition with more body for application, particularly important when creating a French look. The paste was further thickened with 0.1 grams of fumed silica to create an even more sculptable material.

EXAMPLE 37

Trimethyolpropane tris(3-mercaptopropionate), thiol functional material, (10 parts) is mixed with 80 parts of a radiation curable coating of example 13. A thin film of the coating cures to a more tack-free, shiny surface in less than two minutes. The coating is less brittle than the coating of example 13.

EXAMPLE 38

VEctomer 4060, hexanedioic acid, bis{4-(ethenyloxy) butyl} ester, vinyl ether functional material, (8 parts) is mixed with 75 parts of a radiation curable coating of example 13. Rhodia 2076 photoinitiator (0.08 parts) is added to the mixture. A thin film of the coating cures under UV irradiation in less than two minutes.

EXAMPLE 39

Cyracure UVR 6110, cycloaliphatic epoxide, (40 parts), VEctomer 4060 vinyl ether (5 parts) is mixed with 0.20 parts of Rhodia 2076 photoinitiator. This mixture is further mixed with 50 parts of the radiation curable coating of example 13 and irradiated in a thin film. A thin film of the coating cures in less than two minutes to a more tack-free surface with high gloss.

EXAMPLE 40

Isophorone bisurethane bisethylmaleimide (0.25 parts) is blended with 49 parts of BISGMA urethane resin. A thin film of the coating mixture is irradiated and cures in approximately two–three minutes.

EXAMPLE 41

VEctomer 4060 vinyl ether (5 parts) is blended with 30 parts of Example 40. A thin film of the coating is irradiated and cures in approximately 2 minutes.

EXAMPLE 42

Clear silicone molds are used to prepare pre-formed artificial nail tips using the radiation curable compositions of examples 13, 37, 38, 39, 40, and 41. The radiation curable compositions are placed in the molds and cured in the sunlight for several hours. Upon curing, the artificial nail tips are removed from the molds. The artificial nail tips are then glued to natural nails using the procedures previously described and radiation curable coatings of the examples of the present invention are applied. With use, it is found that the radiation curable coatings are less likely to separate or delaminate from the artificial nail tips of this example than from conventional injection molded plastic artificial nail tips and are less likely to be soaked off using the foil/solvent soak-off method.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. A radiation curable nail and/or artificial nail tip coating composition comprising:
   a BISGMA urethane; and
   a photoinitiator;
   said composition comprising a major portion of photopolymerizable resin blend and having a sufficient viscosity to be applied to natural nails and artificial nail tips so that it does not flow off the nails or tips.

2. The composition of claim 1 wherein the photopolymerizable resin blend comprises between approximately 20% and approximately 99% BISGMA urethane.

3. The coating of claim 1 further comprising a second polymer or oligomer.

4. The composition of claim 3 wherein said second polymer comprises a polyol modified methacrylated urethane.

5. The composition of claim 4 wherein;
   said BISGMA urethane comprises between approximately 1% and approximately 30% BISGMA urethane; and
   said polyol modified methacrylated urethane comprises between approximately 1% and approximately 99% polyol modified methacrylated urethane.

6. The composition of claim 1 wherein said photoinitiator comprises at least one member selected from the group consisting of phosphinates, phosphine oxides, sulfanyl ketones, sulfonyl azides, polymeric morpholinkoketones, alpha amino ketones and iodonium hexafluorophosphate salts.

7. A method of increasing soak-off characteristics and susceptibility to polar solvents of a nail coating composition wherein the composition comprises a major portion of photopolymerizable resin blend, the method comprising the steps of:
   providing a nail coating composition comprising a BISGMA urethane resin composition; and
   adding a polymerizable polyol modified methacrylate resin to the composition.

8. A method of increasing the hardness of a cured nail coating composition, the method comprising the steps of:
   providing a nail coating composition; and
   adding a polymerizable BISGMA urethane resin to the nail coating composition prior to curing.

9. The method of claim 8 wherein the step of providing a nail coating composition comprises providing a polymerizable methacrylate resin composition.

10. The method of claim 9 wherein the step of providing a polymerizable methacrylate resin composition comprises providing resins in the composition comprising at least two different molecular weight methacrylate resins.

11. The method of claim 9 wherein the step of providing a resin comprises providing a polyol modified methacrylate resin.

12. The method of claim 9 wherein the step of providing a resin comprises providing a methacrylate urethane resin.

13. A method of applying a soak-off nail coating composition to a coated nail, the method comprising the steps of:
   providing a coated nail;
   applying a composition comprising a polymerizable polyol modified (meth) acrylate resin to the coated nail and;
   curing the applied composition.

14. The method of claim 13 wherein the step of applying a composition comprises providing methacrylate urethane resin.

15. The method of removing a soak-off nail coating composition from a coated nail, the method comprising the steps of:
   providing a nail coated with a non-soak-off radiation cured composition;
   applying a solvent evaporation basecoat composition to the coated nail and allowing the basecoat to dry;

applying a radiation curable composition comprising a polymerizable polyol modified methacrylate resin to the coated nail;

curing the applied composition; and soaking the coated nail with a solvent.

16. The method of claim 15 wherein the step of applying the radiation curable composition comprises applying a clear or colored radiation curable composition to the coated nail.

17. The method of claim 15 wherein the step of soaking the coated nail with a solvent comprises soaking the nail with a solvent and leaving the underlying coated nail intact for further application of radiation curable gel without excessive filing.

18. The method of claim 15 wherein the step of soaking the coated nail with a solvent comprises soaking with a polar solvent.

19. The method of claim 15 wherein the step of providing a nail coated with a non-soak off radiation cured composition comprises providing a composition not able to be soaked off the nail in less than approximately 15 minutes using a foil solvent method.

20. A method of applying a soak-off nail coating composition to a pre-coated nail comprising the steps of:

preparing and providing a coated extended nail;

applying a composition comprising a polyol modified methacrylate urethane resin radiation curable coating, wherein the polyol modified methacrylate urethane resin radiation curable coating is removable or softenable with polar solvents; and curing the composition.

21. The method of claim 20 wherein the step of providing a nail coated with a radiation cured composition comprises providing a cured composition comprising a polymerizable polyol modified (meth) acrylated urethane, a BISGMA urethane, and a photoinitiator.

22. A radiation curable natural nail and/or artificial nail tip coating composition comprising.

a BISGMA urethane;

a polyether, methacrylated urethane;

a photoinitiator; and at least one inhibitor selected from the group consisting of hydroquinone, methyl ether hydroquinone, and butylated hydroxy toluene.

23. The composition of claim 22 further comprising a photoaccelerator.

24. The composition of claim 22 wherein said photoinitiator comprises at least one member selected from the group consisting of phosphinates, phosphine oxides, sulfanyl ketones, sulfonyl azides, polymeric morpholinkoketones, alpha amino ketones and iodonium hexafluorophosphate salts.

25. A composition for making an artificial nail or tip comprising:

a BISGMA urethane;

a second polymer or oligomer; and a photoinitiator;

said composition of a sufficient viscosity to form the artificial nail or tip so that it does not flow off the nail or tip.

26. The composition of claim 25 wherein said second polymer comprises polyol modified methacrylate resin.

27. The composition of claim 25 wherein said photoinitiator comprises at least one member selected from the group consisting of phosphinates, phosphine oxides, sulfanyl ketones, sulfonyl azides, polymeric morpholinkoketones, alpha amino ketones and iodonium hexafluorophosphate salts.

28. A composition for making an artificial nail or tip comprising:

a BISGMA urethane;

a polyol modified methacrylate resin polymer or oligomer; and a photoinitiator;

said composition having increasing soak-off characteristics.

29. A composition for coating a natural nail or for coating or making an artificial nail or tip comprising:

a polyol modified polymerizable methacrylate resin; and a photoinitiator;

said composition coating a natural nail or coating or making an artificial nail or tip;

wherein said photoinitiator comprises at least one member selected from the group consisting of phosphinates, phosphine oxides, sulfanyl ketones, sulfonyl azides, polymeric morpholinkoketones, alpha amino ketones and iodonium hexafluorophosphate salts.

30. The composition of claim 29 further comprising thiol.

31. The composition of claim 29 further comprising cycloalpiphatic epoxide.

32. The composition of claim 29 further comprising maleimide functional materials.

33. A composition for coating a natural nail or for coating or making an artificial nail or tip comprising:

a polymerizable methacrylate resin;

a maleimide functional material; and a photoinitiator.

34. The composition of claim 33 wherein said photoinitiator comprises at least one member selected from the group consisting of phosphinates, phosphine oxides, sulfanyl ketones, sulfonyl azides, polymeric morpholinkoketones, alpha amino ketones and iodonium hexafluorophosphate salts.

35. The composition of claim 33 wherein said polymerizable methacrylate resin comprises BISGMA urethane.

36. A method for reducing loss of adhesion of pre-formed nail tips to radiation curable coatings comprising the steps of:

making a pre-formed radiation curable nail tip out of BISGMA urethane;

applying a coating to the nail from the same BISGMA urethane; and adhering by curing the pre-formed nail tip to the coating.

37. The method of claim 36 wherein the gel comprises a photoinitiator.

38. The composition of claim 37 wherein said photoinitiator comprises at least one member selected from the group consisting of phosphinates, phosphine oxides, sulfanyl ketones, sulfonyl azides, polymeric morpholinkoketones, alpha amino ketones and iodonium hexafluorophosphate salts.

39. A method for applying a coating to a natural or coated nail comprising the steps of:

mixing a radiation curable polymer or oligomer coating comprising a photoinitiator with a commercially available color nail polish;

applying the mixture to the natural or coated nail; and radiation curing the mixture on the natural or coated nail.

40. The method of claim 39 wherein the radiation curable polymer or oligomer comprises a methacrylate resin.

41. The method of claim 40 wherein the methacrylate resin comprises a polyol modified methacrylate resin.

42. The method of claim 40 wherein the methacrylate resin comprises BISGMA urethane.

43. The method of claim 39 wherein said photoinitiator comprises at least one member selected from the group consisting of phosphinates, phosphine oxides, sulfanyl ketones, sulfonyl azides, polymeric morpholinkoketones, alpha amino ketones and iodonium hexafluorophosphate salts.

44. The method of removing a soak-off nail coating composition from a coated nail, the method comprising the steps of:
 providing a nail coated with a non-soak-off radiation cured composition;
 applying a clear or colored radiation curable composition comprising a polymerizable polyol modified methacrylate resin to the coated nail;
 curing the applied composition; and
 soaking the coated nail with a solvent.

45. The method of claim 44 wherein the step of soaking the coated nail with a solvent comprises soaking the nail with a solvent and leaving the underlying coated nail intact for further application of radiation curable gel without excessive filing.

46. The method of claim 44 wherein the step of soaking the coated nail with a solvent comprises soaking with a polar solvent.

47. The method of claim 44 wherein the step of providing a nail coated with a non-soak off radiation cured composition comprises a composition not able to be soaked off the nail in less than approximately 15 minutes using a foil solvent method.

48. The method of removing a soak-off nail coating composition from a coated nail, the method comprising the steps of:
 providing a nail coated with a non-soak-off radiation cured composition;
 applying a radiation curable composition comprising a polymerizable polyol modified methacrylate resin to the coated nail;
 curing the applied composition; and
 soaking the coated nail with a solvent and leaving the underlying coated nail intact for further application of radiation curable gel without excessive filing.

49. The method of claim 48 wherein the step of soaking the coated nail with a solvent comprises soaking with a polar solvent.

50. The method of claim 48 wherein the step of providing a nail coated with a non-soak off radiation cured composition comprises a composition not able to be soaked off the nail in less than approximately 15 minutes using a foil solvent method.

51. The method of removing a soak-off nail coating composition from a coated nail, the method comprising the steps of:
 providing a nail coated with a non-soak-off radiation cured composition;
 applying a radiation curable composition comprising a polymerizable polyol modified methacrylate resin to the coated nail;
 curing the applied composition; and
 soaking the coated nail with a polar solvent.

52. The method of claim 51 wherein the step of providing a nail coated with a non-soak off radiation cured composition comprises a composition not able to be soaked off the nail in less than approximately 15 minutes using a foil solvent method.

53. The method of removing a soak-off nail coating composition from a coated nail, the method comprising the steps of:
 providing a nail coated with a non-soak-off radiation cured composition not able to be soaked off the nail in less than approximately 15 minutes using a foil solvent method;
 applying a radiation curable composition comprising a polymerizable polyol modified methacrylate resin to the coated nail;
 curing the applied composition; and
 soaking the coated nail with a solvent.

* * * * *